United States Patent
Wang et al.

(10) Patent No.: US 11,098,142 B2
(45) Date of Patent: Aug. 24, 2021

(54) OLEFIN POLYMERIZATION CATALYST CARRIER, SOLID CATALYST COMPONENT AND USE THEREOF

(71) Applicant: Renqiu Lihe Technology Ltd., Renqiu (CN)

(72) Inventors: Zhiwu Wang, Renqiu (CN); Shuhang Li, Renqiu (CN); Huashu Li, Renqiu (CN); Junwei Zhang, Renqiu (CN); Hui Zhang, Renqiu (CN); Le Hu, Renqiu (CN); Jinsong Dai, Renqiu (CN); Qingli Ma, Renqiu (CN); Jingyu Wang, Renqiu (CN)

(73) Assignee: Renqiu Lihe Technology Ltd., Renqiu (CN)

( * ) Notice: Subject to any disclaimer, the term of this patent is extended or adjusted under 35 U.S.C. 154(b) by 214 days.

(21) Appl. No.: 16/266,016

(22) Filed: Feb. 2, 2019

(65) Prior Publication Data
US 2019/0169328 A1 Jun. 6, 2019

Related U.S. Application Data

(63) Continuation of application No. 15/662,976, filed on Jul. 28, 2017, now abandoned, which is a (Continued)

(30) Foreign Application Priority Data

Jan. 28, 2015 (CN) .......................... 201510043331.8

(51) Int. Cl.
C08F 110/06 (2006.01)
C08F 4/602 (2006.01)
(Continued)

(52) U.S. Cl.
CPC ............ *C08F 110/06* (2013.01); *C07C 29/70* (2013.01); *C07C 31/28* (2013.01); *C08F 4/02* (2013.01);
(Continued)

(58) Field of Classification Search
CPC .... C08F 4/6024; C08F 4/6094; C08F 4/6224; C08F 4/6294; C08F 4/6425; C08F 4/6494; C08F 4/02
See application file for complete search history.

(56) References Cited

U.S. PATENT DOCUMENTS

2011/0054129 A1* 3/2011 Gupta .................... C07C 29/70
526/123.1

* cited by examiner

*Primary Examiner* — Catherine S Branch
(74) *Attorney, Agent, or Firm* — Yong Chen

(57) ABSTRACT

A method of making an olefin polymerization catalyst carrier with a general structure formula of $Mg(OR^I)_n(OR^{II})_{2-n}$, wherein: $0 \leq n \leq 2$, and $R^I$ and $R^{II}$ can be the same or different and are each independently selected from a $C_1$-$C_{20}$ hydrocarbon group by reacting an alcohol with a metal magnesium powder under the protection of nitrogen in the presence of a halogen or a halogen-containing compound to obtain a first product, and subjecting the product to a treatment pressure of from 0.2 to 5.0 MPa at a treatment temperature of from 80 to 200° C. for a duration of between 2 minutes and 6 hours. Also provided is a method of making an olefin polymerization solid catalyst component which includes the catalyst carrier, a titanium compound, and at least one electron donor compound.

20 Claims, 1 Drawing Sheet

Related U.S. Application Data continuation of application No. PCT/CN2015/077242, filed on Apr. 22, 2015.

(51) Int. Cl.

| | | |
|---|---|---|
| *C08F 4/646* | (2006.01) | |
| *C08F 10/02* | (2006.01) | |
| *C08F 10/00* | (2006.01) | |
| *C08F 4/02* | (2006.01) | |
| *C07C 31/28* | (2006.01) | |
| *C08F 4/645* | (2006.01) | |
| *C08F 4/642* | (2006.01) | |
| *C08F 10/06* | (2006.01) | |
| *C08F 4/622* | (2006.01) | |
| *C07C 29/70* | (2006.01) | |
| *C08F 4/629* | (2006.01) | |
| *C08F 4/609* | (2006.01) | |
| *C08F 4/649* | (2006.01) | |
| *C08F 4/651* | (2006.01) | |
| *C01F 5/00* | (2006.01) | |

(52) U.S. Cl.
CPC .......... *C08F 4/6024* (2013.01); *C08F 4/6094* (2013.01); *C08F 4/6224* (2013.01); *C08F 4/6294* (2013.01); *C08F 4/645* (2013.01); *C08F 4/646* (2013.01); *C08F 4/6425* (2013.01); *C08F 4/6465* (2013.01); *C08F 4/6492* (2013.01); *C08F 4/6494* (2013.01); *C08F 4/651* (2013.01); *C08F 10/00* (2013.01); *C08F 10/02* (2013.01); *C08F 10/06* (2013.01); *C01F 5/00* (2013.01)

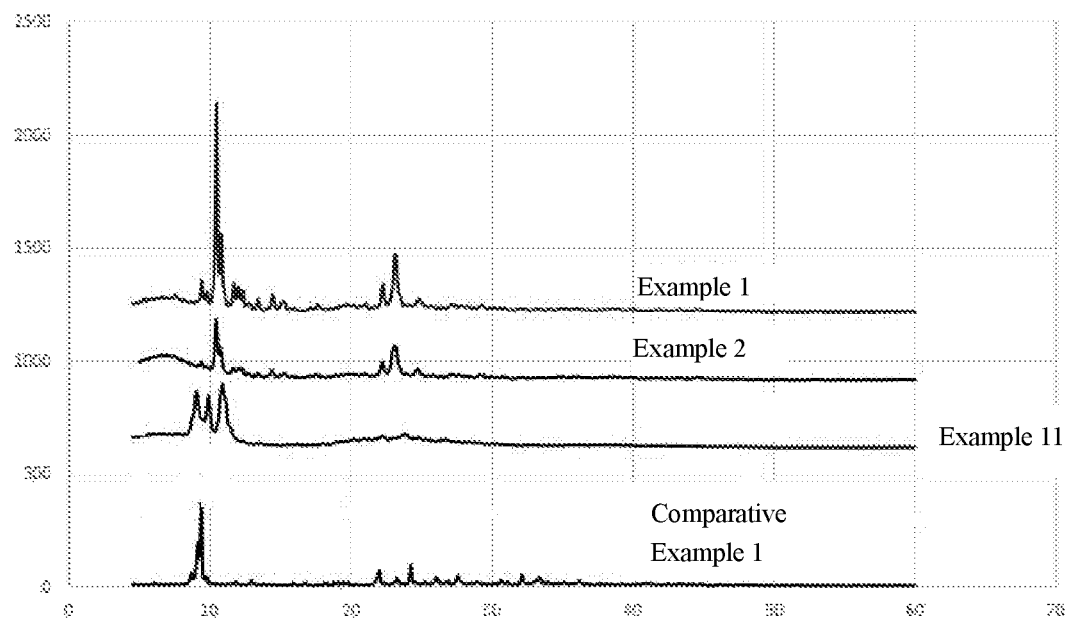

OLEFIN POLYMERIZATION CATALYST CARRIER, SOLID CATALYST COMPONENT AND USE THEREOF

CROSS REFERENCE TO RELATED APPLICATIONS

This application is a continuation of U.S. Nonprovisional application Ser. No. 15/662,976, filed Jul. 28, 2017, which is a continuation of International Patent Application No. PCT/CN2015/077242 filed Apr. 22, 2015, which claims priority to Chinese Application No. 201510043331.8 filed Jan. 28, 2015, the disclosure of each of which is incorporated by reference herein in its entirety.

TECHNICAL FIELD

The present invention relates to an olefin polymerization catalyst carrier, a solid catalyst component and use thereof, and more particularly to an olefin polymerization catalyst carrier and solid catalyst component prepared by use of $Mg(OR^1)_n(OR^2)_{2-n}$ having a specific chemical composition and physical properties, preparation method and use thereof.

BACKGROUND ART

With the continuous development of polyolefin industry, various types of polyolefin catalyst were developed, but widely used effective carrier catalysts for olefin polymerization mainly use magnesium halide as a carrier which are loaded with a heterogenous catalyst of tetravalent titanium compound, and use alkyl aluminum as a co-catalyst.

For the most commonly used polypropylene Ziegler-Natta catalyst, although the final solid catalyst components prepared by different preparation processes are similar, but their differences in microscopic structure can be significant, causing the number of active centers and the distribution of various active centers to vary, therefore the difference in the performance of the catalysts can be significant. The improvement of the catalyst preparation processes mainly involves the use of different Mg source carriers, different preparation processes and optimization of preparation conditions. The carrier plays a key role in controlling the isotacticity and morphology of the polypropylene. On the one hand, the carrier can make $TiCl_4$ dispersed to increase the number of active centers. On the other hand, the carrier can make the active center relatively fixed in position by bonding with the active center and therefore improve the activity of the catalyst.

Over the years, people have paid more attention to the use of different magnesium sources to prepare a magnesium carrier. Common magnesium sources for preparing magnesium carriers mainly include Mg powder, organic magnesium compounds ($MgR_2$, $Mg(OR)_2$, RMgCl, etc.) and inorganic magnesium compounds (such as anhydrous $MgCl_2$). The performance of the catalysts prepared with different magnesium sources can vary. A polyalkene catalyst having a dialkoxymagnesium as the carrier has many distinct advantages (EP 1 209 172 A1, EP 1 270 604 A1, EP 1 260 524A1, EP 1 061 088 A1), the resulting propylene polymers have excellent particle morphology, high stereoregularity, and other desirable properties. In order to obtain this catalyst component for olefin polymerization, it is necessary to prepare a dialkoxymagnesium carrier with excellent properties first. Generally, the Ziegler-Natta catalyst carrier with excellent performance needs to meet the following conditions: a good morphology (e.g., shape, particle size and its distribution), wherein the morphology of the catalyst can be controlled by controlling the particle morphology of the carrier to in turn control the morphology of the polymer; a porous structure and high specific surface area; possessing active groups for loading active catalyst components; and having an appropriate mechanical strength.

Alkoxymagnesium carriers and their use in the preparation of catalyst components for olefin polymerization are well known in the art. CN1810843A describes a method of preparing a catalyst component for olefin polymerization reaction by reacting an alkoxymagnesium carrier with a halogenated transition metal compound. But there is no report about the use of X-ray diffraction pattern to analyze alkoxymagnesium carrier-related crystal material microstructure.

As further described herein, Applicant has found that the $Mg(OR^I)_n(OR^{II})_{2-n}$ carrier having a specific chemical composition and physical properties can be used in a special method to make an olefin polymerization solid catalyst component by reacting the carrier with a titanium compound. The catalyst component may contain at least one electron donor compound. The olefin polymerization catalyst component prepared by using a $Mg(OR^I)_n(OR^{II})_{2-n}$ carrier with specific chemical composition and physical properties can be used to obtain a catalyst with an activity higher than that of the carrier of the prior art, and can be particularly suitable for use in the preparation of olefin polymerization catalysts, which can have better activity than that of the catalyst prepared by the prior art.

SUMMARY OF THE INVENTION

The present invention was made in view of the above-mentioned background art, and an object of the present invention is to provide an olefin polymerization catalyst carrier with a general formula $Mg(OR^I)_n(OR^{II})_{2-n}$.

It is another object of the present invention to provide a method for the preparation of said carrier.

It is also an object of the present invention to provide an olefin polymerization solid catalyst component comprising said carrier.

It is a further object of the present invention to provide a method for the preparation of said olefin polymerization solid catalyst component.

It is a still further object of the present invention to provide a use of the olefin polymerization solid catalyst component in the olefin polymerization.

In order to achieve the object of the present invention, the present invention provides an olefin polymerization catalyst carrier with a general formula $Mg(OR^I)_n(OR^{II})_{2-n}$ (wherein $0 \le n < 2$, and $R^I$ and $R^{II}$ can be the same or different, and are $C_1$-$C_{20}$ hydrocarbon groups). In the X-ray diffraction pattern of the catalyst carrier, there are a set of diffraction peaks in the range of a 2θ diffraction angle of 5°-15°, and the set of diffraction peaks contain 1-4 diffraction peaks. Preferably, there are a set of diffraction peaks in the range of a 2θ diffraction angle of 7°-13°, and the set of diffraction peaks contain 1-4 main diffraction peaks.

Preferably, $R^I$ and $R^{II}$ can be the same or different, and are $C_1$-$C_8$ hydrocarbon groups.

More preferably, the carrier $Mg(OR^I)_n(OR^{II})_{2-n}$ is selected from the group consisting of dimethoxy magnesium, diethoxymagnesium, dipropoxymagnesium, dibutoxymagnesium, ethoxypropoxymagnesium or butoxyethoxymagnesium, etc. More preferably, the carrier is diethoxymagnesium or dipropoxymagnesium.

In the X-ray diffraction pattern of the catalyst carrier, preferably, there are a set of diffraction peaks in the range of a 2θ diffraction angle of 5°-15°, and the set of diffraction peaks contain 1-4 diffraction peaks and there are a second set of diffraction peaks in the range of a 2θ diffraction angle of 20°-30°, and the second set of diffraction peaks contain 1-3 diffraction peaks.

In the X-ray diffraction pattern of the catalyst carrier, preferably, the highest peak of the first set of diffraction peaks corresponds to 2θ diffraction angle of 8°-13°, and the highest peak of the second set of diffraction peaks corresponds to 2θ diffraction angle of 21°-28°.

Further preferably, the highest peak of the first set of diffraction peaks corresponds to 2θ diffraction angle of 9°-12°, and the highest peak of the second set of diffraction peaks corresponds to 2θ diffraction angle of 22°-26°.

Still further preferably, the highest peak of the first set of diffraction peaks corresponds to 2θ diffraction angle of 10°-11°, and the highest peak of the second set of diffraction peaks corresponds to 2θ diffraction angle of 22°-24°.

More preferably, the highest peak of the first set of diffraction peaks corresponds to 2θ diffraction angle of 10.4°±0.2°, and the highest peak of the second set of diffraction peaks corresponds to 2θ diffraction angle of 23.1°±0.2°. Among them, the highest diffraction peak of all peaks is within the range of the first set of peaks.

It is possible, but not strictly necessary, that the carrier of the present invention can also be measured for its particle morphology by electron microscopy. The morphology by electron microscope shows the appearance is a non-spherical solid that is a solid with clear edges and corners.

The present invention also provides a method for preparing an olefin polymerization catalyst carrier comprising reacting an alcohol (A) with a metal magnesium powder (B) in the presence of a halogen or a halogen-containing compound (C) to form a magnesium compound (D), i.e., the carrier. Preferably, the dried or non-dried magnesium compound (D) after the reaction is treated at high temperature and high pressure to obtain a carrier.

Alternatively, an alcohol (A) is reacted with a metal magnesium powder (B) in the presence of a halogen or a halogen-containing compound (C), and is subjected to a high temperature and high pressure continuous treatment to obtain a carrier.

The specific preparation method comprises the following steps:

1) an alcohol (A) is reacted with a metal magnesium powder (B) in the presence of a halogen or a halogen-containing compound (C) to form a magnesium compound (D), the molar ratio of (A) and (B) is from 3 to 5, and the molar ratio of (C) and (B) is from 0.002 to 0.01;

2) when the viscosity of the reaction solution rises sharply, (A) or the inert organic solvent (E) or a mixed solution of (A) and (E) is added, the molar ratio of added amount and (B) is from 2 to 7;

3) after the above reaction is complete, a solid suspension is obtained, or the solvent is filtered off under pressure to give a solid dry powder (D).

Preferably, a step 4) is further comprised: the above-mentioned suspension is added to an autoclave directly, or the above-mentioned dry powder is formulated with the alcohol (A) or the inert organic solvent (E) or a mixture of (A) and (E) into a suspension with a dry powder content of 5% to 80%, and then is added to an autoclave, the reaction was carried out at a temperature higher than 80° C. and a pressure higher than atmospheric pressure, and finally the resulting solid product is dried to obtain a carrier (S).

Alternatively, an alcohol (A) is reacted with a metal magnesium powder (B) in the presence of a halogen or a halogen-containing compound (C) to form a magnesium compound (D), the molar ratio of (A) to (B) is from 3 to 5, and the molar ratio of (C) and (B) is from 0.002 to 0.01; when the viscosity of the reaction solution rises sharply, (A) or an inert organic solvent (E) or the mixture of (A) and (E) is added, the molar ratio of added amount and (B) is from 2 to 7; the above-mentioned reaction system is subjected to a reaction at a temperature higher than 80° C. and a pressure higher than atmospheric pressure, and finally the resulting solid product is dried to obtain a carrier (S).

The alcohol (A) is a lower alcohol having 1 to 6 carbon atoms, which can be used alone or in combination of two or more. In one preferred embodiment, the alcohol is ethanol, so that an olefin polymerization solid catalyst with better polymerization activity, better polymer particle size distribution, and better particle morphology can be obtained. The invention has no strict requirement on the purity of the alcohol, and the water content in the alcohol is generally controlled below 2000 ppm.

The particle size of the metal magnesium powder (B) is preferably 350 μm or less, preferably in the range of 80 to 350 μm, the active magnesium content is more than 98%, and the shape of the metal magnesium powder may be spherical or in other form.

The halogen in the halogen or halogen-containing compound (C) is chlorine, bromine or iodine, and iodine is preferred; the halogen atom of the halogen-containing compound is chlorine, bromine or iodine; in the halogen-containing compound, metal-containing compound is preferred, such as $MgCl_2$, $MgBr_2$, $MgI_2$, $Mg(OEt)Cl$, $Mg(OEt)I$, $CaCl_2$, $NaCl$, $KBr$; particularly preferably $MgCl_2$. The morphology, particle size and the like of these compounds are not particularly limited. These halogen or halogen-containing compounds may be used alone or in combinations.

The inert organic solvent (E) is a liquid aromatic hydrocarbon or alkane at room temperature, where the aromatic hydrocarbon is benzene, toluene, xylene, ethylbenzene, propylbenzene or trimethylbenzene, preferably toluene or xylene, and the alkane is hexane, heptane or cyclohexane; the aromatic hydrocarbon and alkane can be used alone or in combination.

The dried suspension of the prepared carrier (S) or the suspension itself is subjected to a particle morphology test by an electron microscope or a laser particle size tester, the result shows that the magnesium compound carrier (S) prepared by the method of the present invention is non-spherical, which is a square-like shaped carrier with clear edges and corners.

The particle size of the carrier (S) particles is from 1 to 200 μm, preferably 5 to 150 μm, more preferably 10 to 100 μm. Particles less than 5 μm in the particles should not exceed 20%, preferably not more than 10%; particles greater than 100 μm should not exceed 10%, preferably not more than 5%. These particles preferably have a narrow particle size distribution, the more compact the better, the lower content of coarse particles the better.

The conditions in the preparation method according to the present invention are given below:

In step 1), the order of addition of (A), (B) and (C) may be arbitrary, wherein (A) can contact (C) first, and then contact (B); (A), (B) and (C) can be added individually or simultaneously or in batches or continuously, wherein adding in batches or continuously is preferred; the contact temperature of the (A), (B) and (C) is from 30° C. to 90° C., preferably from 40° C. to 80° C.

In step 2), when the viscosity of the reaction solution rises sharply, (A) or an inert organic solvent (E) or a mixed solution of (A) and (E) is added, the molar ratio of added amount and (B) is from 2 to 7; when the mixed solution of (A) and (E) is used, the ratio of (A) and (E) may be arbitrary; when (A) or (E) or the mixture of (A) and (E) is added the temperature is from 30° C. to 90° C., preferably from 40° C. to 80° C.

3) After the above reaction is complete, the resulting solid may be washed with (E), or not be washed to obtain a solid suspension, or the solvent is filtered off under pressure to give a solid dry powder (D).

Preferably, the method further includes a step 4): the above-mentioned suspension is directly added to an autoclave, or the above-mentioned dry powder is formulated with an alcohol (A) or an inert organic solvent (E) or a mixture of (A) and (E) into a suspension with a dry powder content of 5% to 80%, after the resulting suspension is added to an autoclave, the reaction was carried out at a temperature higher than 80° C. and a pressure higher than atmospheric pressure, and finally the resulting solid is dried to obtain a carrier (S).

The reaction pressure is from 0.2 MPa to 5.0 MPa, preferably from 0.3 MPa to 3.0 MPa, most preferably from 0.5 MPa to 2.0 MPa.

The reaction temperature is from 80° C. to 200° C., preferably from 100° C. to 180° C., most preferably from 120° C. to 160° C.

The reaction time is from 2 minutes to 6 hours, preferably from 5 minutes to 5 hours, most preferably from 10 minutes to 4 hours.

The reaction can be carried out with or without stirring.

The carrier has a particle diameter of 1 to 200 μm, preferably 5 to 150 μm, and most preferably 10 to 100 μm. These particles preferably have a narrow particle size distribution, and the smaller amount of large particles the better. Particles having a size less than 5 μm should not exceed 20%, preferably not more than 10%.

The carrier has a non-spherical shape, a cube-like shape with clear edges and corners, and the carrier has a smooth surface and a dense structure. The carrier (D) that has not been subjected to a high temperature and high pressure is spherical, with a crisp surface.

In order to achieve another object of the present invention, provided is an olefin polymerization solid catalyst component which is the reaction product of the above-mentioned carrier $Mg(OR^I)_n(OR^{II})_{2-n}$ with a titanium compound, in which at least one electron donor compound may be contained, wherein $0 \leq n \leq 2$, and $R^I$ and $R^{II}$ can be the same or different, and are $C_1$-$C_{20}$ hydrocarbon groups. In the X-ray diffraction pattern of the carrier, there are a set of diffraction peaks in the range of a 2θ diffraction angle of 5°-15°, and the set of diffraction peaks contain 1-4 main diffraction peaks.

In the carrier $Mg(OR^I)_n(OR^{II})_{2-n}$, $R^I$ and $R^{II}$ can be the same or different, and are preferably $C_1$-$C_8$ hydrocarbon groups. $Mg(OR^I)_n(R^{II})_{2-n}$ is selected from the group consisting of dimethoxy magnesium, diethoxymagnesium, dipropoxymagnesium, dibutoxymagnesium, ethoxypropoxymagnesium or butoxyethoxymagnesium, etc, preferably diethoxymagnesium or dipropoxymagnesium.

In the X-ray diffraction pattern of the carrier $Mg(OR^I)_n(OR^{II})_{2-n}$, preferably, there are a set of diffraction peaks in the range of a 2θ diffraction angle of 7°-13°, and the set of diffraction peaks contain 1-4 main diffraction peaks.

In the X-ray diffraction pattern of the carrier $Mg(OR^I)_n(OR^{II})_{2-n}$, alternatively preferably, there are a set of diffraction peaks in the range of a 2θ diffraction angle of 5°-15°, and the set of diffraction peaks contain 1-4 main diffraction peaks; and there are a second set of diffraction peaks in the range of a 2θ diffraction angle of 20°-30°, and the second set of diffraction peaks contain 1-3 main diffraction peaks. Still further preferably, the highest peak of the first set of diffraction peaks corresponds to 2θ diffraction angle of 8°-13°, and the highest peak of the second set of diffraction peaks corresponds to 2θ diffraction angle of 21°-28°. Still further preferably, in the X-ray diffraction pattern of the carrier $Mg(OR^I)_n(OR^{II})_{2-n}$, the highest peak of the first set of diffraction peaks corresponds to 2θ diffraction angle of 9°-12°, and the highest peak of the second set of diffraction peaks corresponds to 2θ diffraction angle of 22°-26°. More preferably, the highest peak of the first set of diffraction peaks corresponds to 2θ diffraction angle of 10°-11°, and the highest peak of the second set of diffraction peaks corresponds to 2θ diffraction angle of 22°-24°. Most preferably, the highest peak of the first set of diffraction peaks corresponds to 2θ diffraction angle of 10.4° 0.2°, and the highest peak of the second set of diffraction peaks corresponds to 2θ diffraction angle of 23.1°±0.2°.

In the various above embodiments, the highest diffraction peak is within the range of the first set of peaks.

The titanium compound of the present invention has a general formula $TiX_n(OR)_{4-n}$ wherein R is a hydrocarbon group having 1 to 20 carbon atoms, X is a halogen, n=0-4, preferably titanium tetrachloride, titanium tetrabromide, titanium tetraiodide and alkoxy titanium halide, alkyl titanium halide such as methoxy titanium trichloride, ethoxy titanium trichloride, propoxy titanium trichloride, n-butoxy titanium trichloride, dimethoxy titanium dichloride, diethoxy titanium dichloride, dipropoxy titanium dichloride, di-n-butoxy dichloride titanium, trimethoxy titanium chloride, triethoxy titanium chloride, tripropoxy titanium chloride or tri-n-butoxy titanium chloride. These titanium halides can be used alone or in combination. Titanium tetrachloride is most preferably used.

The electron donor compound of the present invention may be selected from Lewis bases containing one or more electronegative groups in which the electron donor atom may be selected from the group consisting of N, O, S, P, As or Sn, preferably from the group consisting of the electron donor compounds such as diethers, esters, diketones and diamine, most preferably selected from the group consisting of: phthalates; or 1,3-diethers; or succinates; or 1,3-diol esters; or a compound containing one or more ether groups or an ester group; these electron donor compounds may be used alone or in combination.

Specifically, one of the electron donor compounds of the present invention is preferably a monocarboxylic acid ester or a polycarboxylic acid ester compound, and specific examples are an aromatic dicarboxylic acid compound and an aliphatic chain dicarboxylic acid ester compound:

Diesters of the aromatic dicarboxylic acids include examples such as phthalic acid diesters or terephthalic acid diesters. Phthalic acid diesters include: dimethyl phthalate, diethyl phthalate, di-n-propyl phthalate, diisopropyl phthalate, di-n-butyl phthalate, diisobutyl phthalate, methyl ethyl phthalate, methyl isopropyl phthalate, methyl n-propyl phthalate, ethyl n-butyl phthalate, ethyl isobutyl phthalate, di-n-pentyl phthalate, diisopentyl phthalate, dihexyl phthalate, di-n-heptyl phthalate, di-n-octyl phthalate, diisooctyl phthalate, di(2,2-dimethylhexyl) phthalate, di(2-ethylhexyl) phthalate, di-n-nonyl phthalate, diisodecyl phthalate, di(2,2-dimethylheptyl) phthalate, n-butyl isohexyl phthalate, n-butyl (2-ethylhexyl) phthalate, n-pentyl n-hexyl phthalate, n-pentyl isononyl phthalate, isopentyl n-decyl phthalate, n-pentyl undecyl phthalate, isopentyl isohexyl phthalate, n-hexyl (2-methylhexyl) phthalate, n-hexyl (2-ethylhexyl) phthalate, n-hexyl isononyl phthalate, n-hexyl (n-decyl) phthalate, n-heptyl (2-ethylhexyl) phthalate, n-heptyl (isononyl) phthalate, n-heptyl neononyl phthalate and 2-ethylhexyl (isononyl) phthalate. These esters may be used alone or in combination. Terephthalic acid diesters include: dimethyl terephthalate, diethyl terephthalate, di-n-propyl terephthalate, diisopropyl terephthalate, di-n-butyl terephthalate, diisobutyl terephthalate, ethyl methyl terephthalate, methyl isopropyl terephthalate, ethyl (n-propyl) terephthalate, ethyl (n-butyl) terephthalate, ethyl (isobutyl) terephthalate, di-n-pentyl terephthalate, diisopentyl terephthalate, dihexyl terephthalate, di-n-heptyl terephthalate, di-n-octyl terephthalate, diisooctyl terephthalate, di(2,2-dimethylhexyl) terephthalate, di(2-ethylhexyl) terephthalate, di-n-nonyl terephthalate, diisononyl terephthalate, diisodecyl terephthalate, di(2,2-dimethylethylheptyl) terephthalate, n-butyl isohexyl terephthalate, n-butyl (2-ethylhexyl) terephthalate, n-pentyl n-hexyl terephthalate, n-pentyl isohexyl terephthalate, isopentyl (heptyl) terephthalate, terephthalic acid, n-pentyl (2-ethylhexyl) terephthalate, n-pentyl (isononyl) terephthalate, isopentyl (n-decyl) terephthalate, n-pentyl undecyl terephthalate, isopentyl isohexyl terephthalate, n-hexyl (2-ethylhexyl) terephthalate, n-hexyl isononyl terephthalate, n-hexyl (n-decyl) terephthalate, n-heptyl (2-ethylhexyl) terephthalate, n-heptyl (isononyl) terephthalate, n-heptyl (neodecyl) terephthalate and 2-ethylhexyl (isononyl) terephthalate. These esters may be used alone or in combination.

Among these diesters, one or more of the following is preferred: diethyl phthalate, dipropyl butyl phthalate, diisopropyl terephthalate, di-n-butyl phthalate, diisobutyl phthalate, di-n-octyl phthalate, diisooctyl phthalate, di-n-butyl terephthalate, diisobutyl terephthalate, di-n-octyl terephthalate, diisooctyl terephthalate, di(2-ethylhexyl) terephthalate, or diisodecyl phthalate.

In the aliphatic chain dicarboxylic acid ester compounds, succinate compounds with the general formula (I) are particularly preferred:

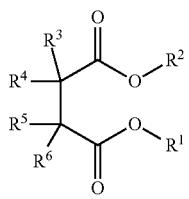

wherein the groups $R^1$ and $R^2$ are the same or different from each other and are $C_1$-$C_{20}$ linear or branched alkyl, alkenyl, cycloalkyl, aryl, aralkyl or alkaryl groups, optionally containing heteroatoms; at least two groups of $R^3$-$R^6$ are different from hydrogen and are selected from $C_1$-$C_{20}$ linear or branched alkyl, alkenyl, cycloalkyl aryl, aralkyl or alkylaryl groups, optionally containing heteroatoms, and the groups $R^3$-$R^6$ may be linked together to form a ring.

$R^1$ and $R^2$ are preferably $C_1$-$C_8$ alkyl, cycloalkyl, aryl, aralkyl and alkaryl groups. Particularly preferred are compounds in which $R^1$ and $R^2$ are selected from primary alkyl groups, especially branched primary alkyl groups. Examples of suitable $R^1$ and $R^2$ are methyl, ethyl, n-propyl, n-butyl, isobutyl, neopentyl, 2-ethylhexyl. Particularly preferred are ethyl, isobutyl and neopentyl.

One of the preferred compound classes described in general formula (I) is such that $R^3$ to $R^5$ are hydrogen and $R^6$ is a branched alkyl, cycloalkyl, aryl, aralkyl, and aralkyl groups having 3 to 10 carbon atoms alkylaryl groups. Particularly preferred are compounds in which $R^6$ is a branched primary alkyl group or a cycloalkyl group having 3 to 10 carbon atoms. Specific examples of suitable monosubstituted succinate compounds are diethyl sec-butylsuccinate, diethyl hexyl succinate, diethyl cyclopropylsuccinate, diethyl norbornyl succinate, diethyl perhydrosuccinate, diethyl trimethyl succinate, diethyl methoxysuccinate, diethyl p-methoxyphenylsuccinate, diethyl p-chlorophenyl succinate, diethyl phenyl succinate, diethyl cyclohexyl succinate, diethyl benzylsuccinate, diethyl cyclohexyl methyl succinate, diethyl t-butyl succinate, diethyl isobutyl succinate, isopropyl succinate, diethyl neopentyl succinate, diethyl isopentyl succinate, diethyl (1-trifluoromethyl ethyl) succinate, diethyl fluorenyl succinate, phenyl succinic acid 1-(ethoxycarbo diisobutyl) phenylsuccinate, diisobutyl sec-butyl succinate, diisobutyl hexylsuccinate, diisobutyl cyclopropylsuccinate, diisobutyl norbornyl succinate, diisobutyl perhydrosuccinate, diisobutyl trimethylsilyl succinate, diisobutyl methoxysuccinate, diisobutyl p-methoxyphenylsuccinate, diisobutyl p-chlorophenoxy succinate, diisobutyl cyclohexylsuccinate, diisobutyl benzylsuccinate, diisobutyl cyclohexylmethyl succinate, diisobutyl t-butyl succinate, diisobutyl isobutyl succinate, diisobutyl isopropyl succinate, diisobutyl neopentylsuccinate, diisobutyl isopentyl succinate, diisobutyl (1-trifluoromethyl ethyl) succinate, diisobutyl fluorenyl succinate, diisobutyl sec-butylsuccinate, di-neopentyl hexyl succinate, di-neopentyl cyclopropyl succinate, di-neopentyl norbornylsuccinate, di-neopentyl perhydrosuccinate, di-neopentyl trimethylsilyl succinate, di-neopentyl p-methoxyphenyl succinate, di-neopentyl p-chlorophenyl succinate, di-neopentyl phenylsuccinate, di-neopentyl cyclohexyl succinate, di-neopentyl benzyl succinate, di-neopentyl cyclohexylmethyl succinate, di-neopentyl t-butyl succinate, di-neopentyl isobutyl succinate, di-neopentyl isopropyl succinate, di-neopentyl neopentyl succinate, di-neopentyl isopentyl succinate, di-neopentyl (1-trifluoromethyl ethyl) succinate, and di-neopentyl fluorenyl succinate.

Other preferred compounds among the compounds with general formula (I) include those compounds that at least two groups of $R^3$ to $R^6$ are different from hydrogen and are selected from $C_1$-$C_{20}$ linear or branched alkyl, alkenyl, cycloalkyl, aryl, aralkyl or alkaryl groups, optionally containing heteroatoms. Particularly preferred are compounds in which two non-hydrogen groups are attached to the same carbon atom. Specific examples of suitable disubstituted succinates are: diethyl 2,2-dimethylsuccinate, diethyl 2-ethyl-2-methylsuccinate, diethyl 2-benzyl-2-isopropyl succinate, diethyl diiso-2-cyclohexylmethyl-2-isobutyl succinate, diethyl 2-cyclopentyl-2-n-butylsuccinate, diethyl 2,2-diisobutyl succinate, diethyl 2-cyclohexyl-2-ethylsuccinate, diethyl 2-isopropyl-2-methylsuccinate, diethyl 2-tetradecyl-2-ethylhexyl succinate, diethyl 2-diisobutyl-2-ethyl succinate, diethyl 2-(1-trifluoromethyl ethyl)-2-methylsuccinate, diethyl 2-isopentyl-2-isobutylsuccinate, diethyl 2-phenyl-2-n-butylsuccinate, diisobutyl 2,2-dimethyl succinate, diisobutyl 2-ethyl-2-methyl succinate, diisobutyl 2-benzyl-2-isopropylsuccinate, diisobutyl 2-cyclohexylmethyl-2-isobutylsuccinate, diisobutyl 2-cyclopentyl-2-n-butylsuccinate, diisobutyl 2,2-diisobutylsuccinate, diisobutyl 2-cyclohexyl-2-ethylsuccinate, diisobutyl 2-isopropyl-2-methyl succinate, diisobutyl 2-tetradecyl-2-ethylsuccinate, diisobutyl 2-isobutyl-2-ethylsuccinate, diisobutyl 2-(1-trifluoromethyl ethyl)-2-methylsuccinate, diisobutyl 2-isopentyl-2-isobutylsuccinate, diisobutyl 2-phenyl-2-n-butylsuccinate, di-neopentyl 2,2-dimethyl succinate, di-neopentyl 2-ethyl-2-methylsuccinate, di-neopentyl 2-benzyl-2-isopropylsuccinate, di-neopentyl 2-cyclohexylmethyl-2-isobutylsuccinate, di-neopentyl 2-cyclopentyl-2-n-butylsuccinate, di-neopentyl 2,2-diisobutylsuccinate, di-neopentyl 2-cyclohexyl-2-ethylsuccinate, di-neopentyl 2-diisopropyl-2-methyl succinate, di-neopentyl 2-tetradecyl-2-ethylsuccinate, di-neopentyl 2-isobutyl-2-ethylsuccinate, di-neopentyl 2-(I-trifluoromethyl ethyl)-2-methylsuccinate, di-neopentyl 2-isopentyl-2-isobutylsuccinate, di-neopentyl 2-phenyl-n-butyl succinate.

In addition, such compounds are particularly preferred in which at least two non-hydrogen groups are attached to different carbon atoms, i.e., $R^3$ and $R^5$ or $R^4$ and $R^6$. Specific examples of suitable compounds are diethyl 2,3-bis(trimethylsilyl) succinate, diethyl 2-sec-butyl-3-methylsuccinate, diethyl 2-(3,3,3-trifluoropropyl)-3-methylsuccinate, diethyl 2,3-bis(2-ethylbutyl) succinate, diethyl 2,3-diethyl-2-isopropyl succinate, diethyl 2,3-diisopropyl-2-methylsuccinate, diethyl 2,3-dicyclohexyl-2-methylsuccinate, diethyl 2,3-dibenzylsuccinate, diethyl 2,3-diisopropylsuccinate, diethyl 2,3-di(cyclohexylmethyl) succinate, diethyl 2,3-di-tert-butylsuccinate, diethyl 2,3-diisobutylsuccinate, diethyl 2,3-di-neopentylsuccinate, diethyl 2,3-diisopentylsuccinate, diethyl 2,3-bis(1-trifluoromethyl ethyl) succinate, diethyl 2,3-di(tetradecyl) succinate, diethyl 2,3-difluorenyl succinate, diethyl 2-tert-butyl-3-isopropylsuccinate, diethyl 2-isopropyl-3-cyclohexylsuccinate, diethyl 2-isopentyl-3-cyclohexyl succinate, diethyl 2-tetradecyl-3-cyclohexylsuccinate, diethyl 2-cyclohexyl-3-cyclopentylsuccinate, diethyl 2,2,3,3-tetramethylsuccinate, diethyl 2,2,3,3-tetraethylsuccinate, diethyl 2,2,3,3-tetrapropylsuccinate, diethyl 2,3-diethyl-2,3-diisopropylsuccinate, diethyl 2,2,3,3-tetrafluorosuccinate, diisobutyl 2,3-bis(trimethylsilyl) succinate, diisobutyl 2-sec-butyl-3-methylsuccinate, diisobutyl 2-(3,3,3-trifluoropropyl)-3-methylsuccinate, diisobutyl 2,3-di(2-ethylbutyl) succinate, diisobutyl 2,3-diethyl-2-isopropylsuccinate, diisobutyl 2,3-diisopropyl-2-methylsuccinate, diisobutyl 2,3-dicyclohexyl-2-methylsuccinate, diisobutyl 2,3-dibenzylsuccinate, diisobutyl 2,3-diisopropylsuccinate, diisobutyl 2,3-di(cyclohexylmethyl) succinate, diisobutyl 2,3-di-tert-butylsuccinate, diisobutyl 2,3-diisobutylsuccinate, diisobutyl 2,3-di-neopentylsuccinate, diisobutyl 2,3-diisopentyl succinate, diisobutyl 2,3-bis(1-trifluoromethyl ethyl) succinate, diisobutyl 2,3-di(tetradecyl) succinate, diisobutyl 2,3-difuorenyl succinate, diisobutyl 2-isopropyl-3-isobutylsuccinate, diisobutyl 2-tert-butyl-3-isopropylsuccinate, diisobutyl 2-isopropyl-3-cyclohexyl succinate, diisobutyl 2-isopentyl-3-cyclohexylsuccinate, diisobutyl 2-tetradecyl-3-cyclohexylmethylsuccinate, diisobutyl 2-cyclohexyl-3-cyclopentylsuccinate, diisobutyl 2,2,3,3-tetramethyl succinate, diisobutyl 2,2,3,3-tetraethylsuccinate, diisobutyl 2,2,3,3-tetrapropyl succinate, diisobutyl 2,3-diethyl-2,3-dipropylsuccinate, diisobutyl 2,2,3,3-tetrafluorosuccinate, di-neopentyl 2,3-bis(trimethylsilyl) succinate, di-neopentyl 2-sec-butyl-3-methylsuccinate, di-neopentyl 2-(3,3,3-trifluoropropyl)-3-methylsuccinate, di-neopentyl 2,3-di (2-ethylbutyl) succinate, di-neopentyl 2,3-diethyl-2-isopropylsuccinate, di-neopentyl 2,3-diisopropyl-2-methylsuccinate, di-neopentyl 2,3-dicyclohexyl-2-methylsuccinate, di-neopentyl 2,3-dibenzyl succinate, di-neopentyl 2,3-diisopropylsuccinate, di-neopentyl 2,3-bis (cyclohexylmethyl) succinate, di-neopentyl 2,3-di-t-butylsuccinate, di-neopentyl 2,3-diisobutylsuccinate, di-neopentyl 2,3-di-neopentylsuccinate, di-neopentyl 2,3-(1-trifluoromethyl ethyl) succinate, di-neopentyl 2,3-di(tetradecyl)succinate, di-neopentyl 2,3-difluorenylsuccinate, di-neopentyl 2-isopropyl-3-isobutylsuccinate, di-neopentyl 2-tert-butyl-3-isopropylsuccinate, di-neopentyl 2-isopropyl-3-cyclohexyl succinate, di-neopentyl 2-isopentyl-3-cyclohexyl succinate, di-neopentyl 2-tetradecyl-3-cyclohexylmethylsuccinate, di-neopentyl 2-cyclohexyl-3-isopentyl succinate, di-neopentyl 2,2,3,3-tetramethyl succinate, di-neopentyl 2,2,3,3-tetraethylsuccinate, di-neopentyl 2,2,3,3-tetrapropylsuccinate, di-neopentyl 2,3-diethyl-2,3-diisopropylsuccinate, di-neopentyl 2,2,3,3-tetrafluorosuccinate.

As mentioned above, the compounds represented by the general formula (I) in which two or four groups $R^3$ to $R^6$ bonded to the same carbon atom are bonded together to form a ring are also preferred. Specific examples of suitable compounds are 1-(ethoxycarbonyl)-1-(ethoxyacetyl)-2,6-dimethylcyclohexane, 1-(ethoxycarbonyl)-1-(ethoxyacetyl)-2,5-dimethylcyclopentane, 1-(ethoxycarbonyl)-1-(ethoxyacetylmethyl)-2-methylcyclohexane, 1-(ethoxycarbonyl)-1-(ethoxyacetylcyclohexyl) cyclohexane.

The above-mentioned compounds may be used in the form of pure isomers or in the form of mixtures of enantiomers, or in the form of mixtures of positional isomers and enantiomers. When pure isomers are used, they are generally isolated using conventional techniques known in the art. In particular, some of the succinic acid esters of the present invention may be used in pure racemic or meso form, or alternatively in both forms of mixtures.

The electron donor compound of the present invention may also be selected from 1,3-propanediether compounds represented by the general formula (II):

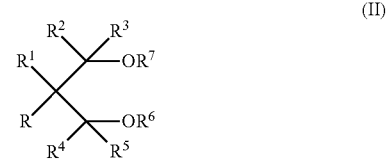

(II)

wherein R, $R^1$, $R^2$, $R^3$, $R^4$ and $R^5$ may be the same or different and represent a H or a linear or branched alkyl, cycloalkyl, aryl, alkaryl or aralkyl group having from 1 to 18 carbon atoms; $R^6$ and $R^7$ may be the same or different and represent linear or branched alkyl groups having 1 to 20 carbon atoms, cycloalkyl groups having 3 to 20 carbon atoms, aryl groups having 5 to 20 carbon atoms, alkylaryl groups and aralkyl groups having 7-20 carbon atoms; one or more groups in R-$R^7$ may be linked to form a ring structure, and may comprise one or more heteroatoms selected from the group consisting of halogen, N, O, S, P and Si.

Specific examples of ethers which can be advantageously used include 2-(2-ethylhexyl) 1,3-dimethoxypropane, 2-isopropyl-1,3-dimethoxypropane, 2-butyl-1,3-dimethoxypropane, 2-sec-butyl-1,3-dimethoxypropane, 2-cyclohexyl-1,3-dimethoxypropane, 2-phenyl-1,3-dimethoxypropane, 2-tert-butyl-1,3-dimethoxypropane, 2-cumyl-1,3-dimethoxypropane, 2-(2-phenylethyl) 1,3-dimethoxypropane, 2-(2-cyclohexylmethyl)-1,3-dimethoxypropane, 2-(p-chlorophenyl)-1,3-dimethoxypropane, 2-(diphenylmethyl)-1,3-dimethoxypropane, 2(1-naphthyl)-1,3-dimethoxypropane, 2(p-fluorophenyl)-1,3-dimethoxypropane, 2 (1-decahydronaphthyl)-1,3-dimethoxypropane, 2(p-tert-butylphenyl)-1,3-dimethoxypropane, 2,2-dicyclohexyl-1,3-dimethoxypropane, 2,2-diethyl-1,3-dimethoxypropane, 2,2-dipropyl-1, 3-dimethoxypropane, 2,2-dibutyl-1,3-dimethoxypropane, 2,2-diethyl-1,3-diethoxypropane, 2,2-dicyclopentyl-dimethoxypropane, 2,2-dipropyl-1,3-diethoxypropane, 2,2-dibutyl-1,3-diethoxypropane, 2-methyl-2-ethyl-1,3-dimethoxypropane, 2-methyl-2-propyl-1,3-dimethoxypropane, 2-methyl-benzyl-1,3-dimethoxypropane, 2-methyl-2-phenyl-1,3-dimethoxypropane, 2-methyl-2-cyclohexyl-1,3-dimethoxypropane, 2-methyl-2-methylcyclohexyl-1,3-dimethoxypropane, 2,2-bis(p-chlorophenyl)-1,3-dimethoxypropane, 2,2-bis(2-phenylethyl)-1,3-dimethoxypropane, 2,2-bis(2-cyclohexylethyl)-1,3-dimethoxypropane, 2-methyl-2-isobutyl-1,3-dimethoxypropane, 2-methyl-2-(2-ethylhexyl)-1,3-dimethoxypropane, 2,2-bis(2-ethylhexyl)-1,3-dimethoxypropane, 2,2-bis(p-methylphenyl)-1,3-dimethoxypropane, 2-methyl-2-isopropyl-3-dimethoxypropane, 2,2-diisobutyl-1,3-dimethoxypropane, 2,2-diphenyl-1,3-dimethoxypropane, 2,2-benzyl-1,3-dimethoxypropane, 2-isopropyl-2-cyclopentyl-1,3-dimethoxypropane, 2,2-bis(cyclohexylmethyl)-1,3 dimethoxypropane, 2,2-diisobutyl-1,3-diethoxypropane, 2,2-diisobutyl-1,3-dibutyloxypropane, 2-isobutyl-2-isopropyl-1,3-dimethoxypropane, 2,2-di-sec-butyl-1,3-dimethoxypropane, 2,2-di-t-butyl-1,3-dimethoxypropane, 2,2-neopentyl-1,3-dimethoxypropane, 2-isopropyl-2-isopentyl-1,3-dimethoxypropane, 2-phenyl-2-benzyl-1,3-dimethoxypropane, 2-cyclohexyl-2-cyclohexylmethyl-1,3-dimethoxypropane, 1,1-bis(methoxymethyl)cyclopentadiene; 1,1-bis(methoxymethyl)-2,3,4,5-tetramethylcyclopentadiene; 1,1-bis(methoxymethyl)-2,3,4,5-tetraphenylcyclopentadiene; 1,1-bis(methoxymethyl)-2,3,4,5-tetrafluorocyclopentadiene; 1,1-bis(methoxy methyl)-3,4-dicyclopentylcyclopentadiene; 1,1-bis(methoxymethyl)indene; 1,1-bis(methoxymethyl)-2,3-dimethylindene; 1,1-bis(methoxymethyl)-4,5,6,7-tetrahydroindene; 1,1-bis(methoxymethyl)-2,3,6,7-tetrafluoroindene; 1,1-bis(methoxymethyl)-4,7-dimethylindene; 1,1-bis(methoxymethyl)-3,6-dimethylindene; 1,1-bis(methoxymethyl)-4-phenylindene; 1,1-bis(methoxymethyl)-4-phenyl-2-methyl indene; 1,1-bis(methoxymethyl)-4-cyclohexylindene; 1,1-bis(methoxymethyl)-7-(3,3,3-trifluoropropyl) indene; 1,1-bis(methoxymethyl)-7-trimethylsilylindene; 1,1-bis(methoxymethyl)-7-trifluoromethylindene; 1,1-bis(methoxymethyl)-4,7-dimethyl-4,5,6,7-tetrahydroindene; 1,1-bis(methoxymethyl)-7-methylindene; 1,1-bis(methoxymethyl)-7-cyclopentylindene; 1,1-bis(methoxymethyl)-7-isopropylidene; 1,1-bis(methoxymethyl)-7-cyclohexylindene; 1,1-bis(methoxymethyl)-7-tert-butylidene; 1,1-bis(methoxymethyl)-7-tert-butyl-2-methylindene; 1,1-bis(methoxymethyl)-7-phenylindene; 1,1-bis(methoxymethyl)-2-phenylindene; 1,1-bis(methoxymethyl)-1H-benzo[e]indene; 1,1-bis(methoxymethyl)-1H-2-methylbenzo[e]indene; 9,9-bis(methoxymethyl)fluorene; 9,9-bis(methoxymethyl)-2,3,6,7-tetramethylfluorene; 9,9-bis(methoxymethyl)-2,3,4,5,6,7-hexafluorofluorene; 9,9-bis(methoxymethyl)-2,3-benzofluorene; 9,9-bis(methoxymethyl)-2,3,6,7-dibenzofluorene; 9,9-bis(methoxymethyl)-2,7-diisopropylfluorene; 9,9-bis(methoxymethyl)-1,8-dichlorofluorene; 9,9-bis(methoxymethyl)-2,7-dicyclopentylfluorene; 9,9-bis(methoxymethyl)-1,8-difluorofluorene; 9,9-bis(methoxymethyl)-1,2,3,4-tetrahydrofluorene; 9,9-bis(methoxymethyl)-1,2,3,4,5,6,7,8-octahydrofluorene; 9,9-bis(methoxymethyl)-4-tert-butylfluorene.

A further preferred compound of the electron donor compound of the present invention is a diol ester compound with the general formula (III):

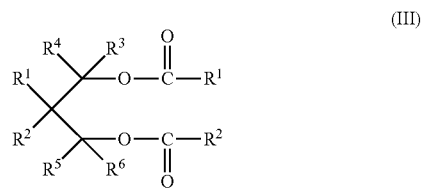

wherein $R^3$ to $R^6$ and $R^1$ to $R^2$ are the same or different hydrogen, halogen or a substituted or unsubstituted linear or branched $C_1$-$C_{20}$ alkyl group, a $C_3$-$C_{20}$ cycloalkyl group, a $C_6$-$C_{20}$ aryl group, a $C_7$-$C_{20}$ alkaryl group, a $C_7$-$C_{20}$ aralkyl group, a $C_2$-$C_{10}$ alkenyl group or a $C_{10}$-$C_{20}$ fused ring aryl group; but when $R^1$ and $R^2$ are not hydrogen, one or more of $R^3$-$R^6$ and $R^1$-$R^2$ optionally form a ring or not.

Specific examples of the diol ester compounds include 1,3-propanediol dibenzoate, 2-methyl-1,3-propanediol dibenzoate, 2-ethyl-1,3-propanediol dibenzoate, 2-propyl-1,3-propanediol dibenzoate, 2-butyl-1,3-propanediol dibenzoate, 2,2-dimethyl-1,3-propanediol dibenzoate, 2-ethyl-2-butyl-1,3-propanediol dibenzoate, 2,2-diethyl-1,3-propanediol dibenzoate, 2-methyl-2-propyl-1,3-propanediol dibenzoate, 2-isopropyl-2-isopentyl-1,3-propanediol dibenzoate, 2,4-pentanediol dibenzoate, 3-methyl-2,4-pentanediol dibenzoate, 3-ethyl-2,4-pentanediol dibenzoate, 3-propyl-2,4-pentanediol dibenzoate, 3-butyl-2,4-pentanediol dibenzoate, 3,3-dimethyl-2,4-pentanediol dibenzoate, 2-methyl-1,3-pentanediol dibenzoate, 2,2-dimethyl-1,3-pentanediol dibenzoate, 2-ethyl-1,3-pentanediol dibenzoate, 2-butyl-1,3-pentanediol dibenzoate, 2-methyl-1,3-pentanediol dibenzoate, 2-ethyl-1,3-pentanediol dibenzoate, 2-propyl-1,3-pentanediol dibenzoate, 2-butyl-1,3-pentanediol dibenzoate, 2,2-dimethyl-1,3-pentanediol dibenzoate, 2-methyl-1,3-pentanediol dibenzoate, 2,2-dimethyl-1,3-pentanediol dibenzoate, 2-ethyl-1,3-pentanediol dibenzoate, 2-butyl-1,3-pentanediol dibenzoate, 2,2,4-trimethyl-1-pentanediol dibenzoate, 3-methyl-3-butyl-2,4-pentanediol dibenzoate, 2,2-dimethyl-1,5-pentanediol dibenzoate, 3,5-heptanediol dibenzoate, 4-ethyl-3,5-heptanediol dibenzoate and the like. Preferred are pentanediol esters and heptanediol esters.

A further preferred compound of the electron donor compound of the present invention is a ring-substituted compound containing an ether group and an acid ester group selected from the group consisting of the compounds represented by the general formula (IV):

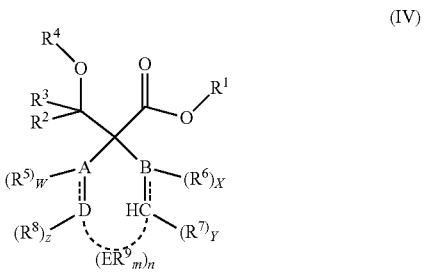

Wherein, A, B, C, D, and E are each carbon atoms, or are selected from N, O and S heteroatoms; W, X, Y, Z, and m are 0, 1 or 2; with the proviso that when n is equal to 0:

I) B is a nitrogen atom, A, C and D are each carbon atoms, X is 1, W, Y and Z are each 2; or II) C is a nitrogen atom, A, B and D are each carbon atoms, Y is 1, W. X and Z are each 2; or III) C is an oxygen atom, A, B, and D are each carbon atoms, Y is 0, W, X and Z are each 2; or IV) A and C are each oxygen atoms, W and Y are each 0, X and Z are each 2; or V) B is an oxygen atom, A, C and D are each carbon atoms, X is 0, W, Y and Z are each 2; or VI) A, B, C and D are each carbon atoms and bonded to each other through a single bond, W, X, Y and Z are each 2; or VII) A, B, C and D are each carbon atoms, B and C are bonded through a double bond, X and Y are each 1, W and Z are each 2; or VIII) A, B, C and D are each carbon atoms, A and D, B and C, respectively are bonded through a double bond, W, X, Y and Z are each 1;

when n is equal to 1:

i) D is a nitrogen atom, A, B, C, and E are each carbon atoms, Z is 1, W, X, Y, and m are each 2; or ii) E is a nitrogen atom, A, B, C and D are each carbon atoms, m is 1, W, X, Y and Z are each 2; or iii) E is an oxygen atom, A, B, C and D are each carbon atoms, m is 0, W, X, Y and Z are each 2; or iv) C and D are each oxygen atoms, A, B and E are each carbon atoms, Y and Z are each 0, W, X, and m are each 2; or v) D is an oxygen atom, A, B, C, and E are each carbon atoms, Z is 0, W, and in are each 2; or vi) B is an oxygen atom, A, C, D, and E are each carbon atoms, X is 0, W, Y, Z, and in are each 2;

vii) A, B, C, D, and E are each carbon atoms, W, X, Y Z, and m are each 2;

viii) A, B, C, D, and E are each carbon atoms, B and C are bonded through a double bond, X and Y are each 1, W, Z, and m are each 2; or ix) A, B, C, D, and E are each carbon atoms, A and D, B and C, respectively, are bonded through a double bond, W, X, Y and Z are each 1, m is 2;

when n is equal to 2:

A and B are each carbon atoms, W and X are each 2, C and D are each a carbon atom, sulfur atom, oxygen atom or nitrogen atom, Y and Z are each 2 or 0, E represents two carbon atoms bonded through a single bond or a double bond, where when the two carbon atoms of E are bonded through a double bond, m is equal to 1, and when the two carbon atoms of E are bonded through a single bond, m is equal to 2;

$R^1$ and $R^4$ are same or different $C_1$-$C_{20}$ hydrocarbon groups, such as $C_1$-$C_{20}$ linear or branched alkyl, alkenyl, $C_3$-$C_{20}$ cycloalkyl, $C_6$-$C_{20}$ aryl, $C_7$-$C_{20}$ alkaryl and $C_7$-$C_{20}$ aralkyl group; $R^2$, $R^3$, $R^5$-$R^9$ are same or different, and are each selected from a hydrogen atom, halogen atom, oxygen atom, sulfur atom and $C_1$-$C_{20}$ hydrocarbon group, such as $C_1$-$C_{20}$ linear or branched alkyl, $C_3$-$C_{20}$ cycloalkyl, $C_6$-$C_{20}$ aryl, $C_7$-$C_{20}$ alkaryl and $C_7$-$C_{20}$ aralkyl group;

Said $R^1$-$R^9$ each may optionally contain one or more R atoms as a substituent of a carbon atom or hydrogen atom, or both, where R is a heteroatom, a linear or branched $C_1$-$C_{20}$ alkyl, $C_3$-$C_{20}$ cycloalkyl, $C_6$-$C_{20}$ aryl, $C_7$-$C_{20}$ alkaryl and $C_7$-$C_{20}$ aralkyl group; wherein any two groups of $R^1$-$R^9$ may be bonded to each other to generate one or more Spiro ring or fused ring structures.

The examples of the compounds included in the general formula (IV) are listed as follows:

Ethyl 1-(1,1-vinyldioxyethyl)cyclopentane-1-carboxylate; ethyl 2-(1-methoxycyclopentane)-2-methoxy acetate; methyl 1-(methoxymethyl)cyclopentane carboxylate; methyl 1-(benzyloxymethyl)cyclohexyl carboxylate; ethyl 1-(4,4,6-trimethyl-[1,3]azapyran-2-yl)-cyclopentyl carboxylate; methyl 2-chloro-methoxyethyl-1-cyclopentyl carboxylate; bi(cyclohexyl carboxylic acid methyl ester)methyl methyl ether; ethyl 2-benzyloxy-(1,1-vinyldioxyethyl)cyclopentyl carboxylate; dimethyl-1-methoxybicyclo[2.2.2]oct-8-ene-2,6-dicarboxylic acid methyl ester; 1-methoxybicyclo[2.2.2]oct-9-ane, trimethyl-1-methoxybicyclo[2.2.1]heptane-2,6,10-tricarboxylate; 1-methoxy-1-cyclopentane carboxylic acid ethyl ester-3-phenyl-propylene; 2-benzyloxymethyl-2-ethoxycarbonyl-1-(tetrahydropyran-2-oxy) oxocyclopentane; 2-benzyloxy-2-ethoxycarbonyl-cyclopentanol; methyl 1-(1-methoxyethypcyclopentane carboxylate; 2-methyl 2-(1-cyclopentyl carboxylic acid ethyl ester-1-yl)-4-methylene-1,3-oxopropane; methyl-(3,4-dihydro-1H-isopyran-1-yl) cyclopentyl carboxylate; ethyl 1-(methoxymethyl)cyclopentane carboxylate; methyl-1-(ethoxymethyl) cyclopentane carboxylate; 2-benzyloxymethyl-1-cyclopentanonecarboxylic acid ethyl ester; methyl 1-benzyloxymethyl-pyrrolidine-2-carboxylate; methyl-hexahydro-2,2,7-trimethyl-6-oxo [1,3]dioxo[5,4-b]pyrrole-4a-carboxylate; methyl-2-benzyloxymethyl-5-carbonylpyrrolidine-2-carboxylate; methyl-1-(4-chlorophenyl)-3-(methoxymethyl)-4,5-dicarbonylpyrrole-3-carboxylate; methyl 3-methoxymethyl-pyrrolidine-3-carboxylate; 1-tert-butoxycarbonylmethyl-3-methoxymethyl-pyrrolidine-3-carboxylate; methyl 1-benzyl-3-methoxymethyl-pyrrolidine-3-carboxylate; 2-ethoxymethyl-pyrrolidine-1,2-dicarboxylic acid 1-tert-butyl ester 2-methyl ester; 2-isopropoxymethyl-pyrrolidine-1,2-dicarboxylic acid 1-tert butyl ester 2-ethyl ester; methyl 3-methoxymethyl-1-(3-methylphenyl)-4,5-dicarbonylpyrrolidine-3-carboxylate; methyl 3-methoxy-1-(4-fluorophenyl)-4,5-dicarbonylpyrrolidine-3-carboxylate; methyl 3-methoxymethyl-1-(4-bromophenyl)-4,5-dicarbonylpyrrolidine-3-carboxylate; methyl 1-(4-hydroxyphenyl)-3-methoxymethyl-4,5-dicarbonylpyrrolidine-3-carboxylate; ethyl 3-ethoxymethyl-1-phenyl-4,5-dicarbonylpyrrolidine-3-carboxylate; ethyl 3-ethoxymethyl-1-(3-methylphenyl)-4,5-dicarbonylpyrrolidine-3-carboxylate; ethyl 3-methoxymethyl-2-carbonyl-tetrahydrofuran-3-carboxylate; ethyl 3-isopropoxymethyl-2-carbonyl-tetrahydrofuran-3-carboxylate; ethyl 1-(4,4,6-trimethyl-[1,3] oxazin-2-yl)-cyclopentyl carboxylate; methyl-3-ethyl-2-[(2-trimethylsilylethoxy) methoxymethyl]1,4-dioxaspiro[4.4]nonane-2-carboxylate; methyl 5-oxo-phenyl-2-deoxy-4-methoxycarbonyl-D-pentofuranoside; 2-benzyloxymethyl-3-(2-methoxyvinyl)-2-methoxycarbonyl-1,4-oxaspiro[4.4]nonane; 4-pentenyl-5-O-benzyl-2-deoxy-4-methoxycarbonyl-D-pentofuranoside; methyl 5-O-benzyl-3-O-(t-butyldimethylsilane)-2-deoxy-4-methoxycarbonyl-D-pentofuranoside; 1-(2-benzyloxymethyl-3-hydroxy-2-methoxycarbonyl-5-tetrahydrofuran)thymine; 4-N-acetyl-1-(2-benzyloxymethyl-3-hydroxy-2-methoxycarbonyl-5-tetrahydrofuran) cytosine; 4-N-acetyl-5-O-benzyl-2-deoxy-4-methoxycarbonyl-cytosine; methyl-3,3-dimethyl-8-[5-methyl-2 (1-H), 4-(3H)-dioxopyridine-1-yl]-2,4-dioxabicyclo[4.3.0]non-6-carboxylate; methyl-1-(4-methoxybenzyl)-2-benzyloxymethyl-3-hydroxy-3-methyl-4-methylene-5-pyrrolidin-2-carb aldehyde; methyl 2-(hydroxymethoxymethyl)1-methoxy-5-carbonylpyrrolidin-2-carboxylate; ethyl (2-cyclopentyl-[1,3]dioxolan-2-)-1-ethyl-2-oxa-2,3-dihydro-1H-indole-3-carboxylate; benzyloxycarbonyl-thioprolyl-thioproline diethyl acetal; benzyloxycarbonyl-thioprolyl-thioproline dibutyl acetal; benzyloxycarbonyl-thiprolyl-thioproline dimethyl acetal; methyl-2-(benzyloxymethyl)-3-hydroxy-4-methylene-5-carbonylpyrrolidine-2-carboxylate; 1-tert-butyl-2-methyl-2-(benzyloxymethyl)-5-oxo-pyrrolidine-1,2-dicarboxylate; methyl-2-benzyloxymethyl-3-tertbutyldimethylsilyloxy-4-methyl-5-carbonylpyrrolidine-2-carboxylate; 1-tert-butyl-2-methyl-2(benzyloxymethyl)-3-hydroxy-4-methylene-5-oxopyrrolidine-1,2-dicarboxylate; 5-tert-butyl-6-methyl-6-(benzyloxymethyl)-2-methyl-4-oxohexahydro-5H-pyrrolo[3,4-d]oxazole-5,6-dicarboxylate; methyl-1-(3,4-dihydro-1H-isobenzo-1-yl)cyclopentane carboxylate; tert-butyl-1-(1-ethoxy-3-phenyl-allyl)-2-carbonylcyclopentane carboxylate; 1-tert-butyl-2-methyl-2 (benzyloxymethyl) pyridine-1,2-dicarboxylate; N-(t-butoxycarbonyl)-α-(methoxymethyl) proline ethyl ester; N-(t-butoxycarbonyl)-α-(t-butylmethyl)proline ethyl ester; 1-tert-butyl-2-methyl-2-(benzyloxymethyl)pyrrolidine-1,2-dicarboxylate; methyl 3-benzyloxymethyl-1-(2,6-dimethylphenyl)-5-oxo-pyrrolidine-3-carboxylate; ethyl 1-benzyl-2-(diethoxymethyl)pyrrolidine-2-carboxylate; methyl 2-benzyloxymethyl-1-methyl-pyrrolidine-2-carboxylate;

9-methoxymethyl-fluorene carboxylic acid-(9)-methyl ester; 9-ethoxymethyl-fluorene carboxylic acid-(9)-methyl ester; 9-methoxymethyl-fluorene carboxylic acid-(9)-ethyl ester; 9-methoxymethyl-fluorene carboxylic acid-(9)-n-butyl ester; 9-methoxymethyl-fluorene carboxylic acid-(9)-isobutyl ester; 9-methoxymethyl-fluorene carboxylic acid-(9)-isopropyl ester; 9-ethoxymethyl-fluorene carboxylic acid-(9)-ethyl ester; 9-ethoxymethyl-fluorene carboxylic acid-(9)-n-butyl ester; 9-ethoxymethyl-fluorene carboxylic acid-(9)-isobutyl ester; 9-ethoxymethyl-fluorene carboxylic acid-(9)-isopropyl ester; bi(9-methoxy carbonyl-fluoren-9-yl)-ether; methyl 3-[1-[2-(indol-3-yl)-1-oxo-ethyl]]-2-methoxy-3-azabicyclo[3.2.1]oct-6-ene-7-ethyl-1-carboxylate; methyl-2-methoxydibenzobicyclo-[3.2.1]octadien-1-carboxylate; methyl-benzyloxymethyl-2-cyclopent-2-ene-1-carboxylate; methyl-4-[(tert-butoxycarbonyl)amino]-1-ethoxymethyl-cyclopent-2-ene-1-carboxylate; 8-benzyloxy-1-ethoxycarbonyl-5,7,7-trimethyl-2-(propan-2-ylidene)bicyclo[3.3.0]oct-2-ene; methyl-1,1-bis(hydroxymethyl)-3-methoxy-1,2,3,3a,6,6a-hexahydropentene-3a-carboxylate; methyl-1-(t-butyldimethylsiloxymethyl)-1-di(hydroxymethyl)-3-methoxy-1,2,3,3a,6,6a-hexahydropentene-3a-carboxylate; methyl 1,1-bis(benzyloxymethyl)-3-methoxy-1,2,3,3a,6,6a-hexahydropentene-3a-carboxylate; 1,2,3,4,5-pentamer (methoxycarbonyl)-5-(methoxy methyl) cyclopentadiene;

Methyl benzyloxymethyl-cyclohexylcarboxylate; ethyl 8-benzyloxymethyl-1,4-dioxo-spiro[4,5]decane-8-carboxylate; 2-benzyloxymethyl-2-ethoxycarbonylcyclohexanol; 2-benzyloxymethyl-2-ethoxycarbonyl-1-(tetrahydrofuran-2-yl) oxycyclohexane; methyl 4-(1,3-dioxolane-2-yl)-(1,1'-dicyclohexyl)-4-carboxylate; ethyl-1-(benzyloxymethyl)-4,4-difluorocyclohexanecarboxylate; ethyl 6-methoxymethyl-1,4-dioxa-spiro[4.5]decane-6-carboxylate; 2-methoxymethyl-2-ethoxycarbonyl-6-methylcyclohexanol; ethyl 1-diethoxymethyl-cyclohexylcarboxylate; methyl methoxymethyl-cyclohexylcarboxylate; methyl spiro<bicyclo<3.3.1>nonane-2,2'-<1.3>dioxa-2,2'-[1.3]dioxolane>1-butyrate; ethyl 1-benzyloxymethyl-4-dimethoxycyclohexyl-carboxylate; ethyl benzyloxymethyl-4-methoxycyclohexyl-carboxylate; ethyl-4-methyl-1-methoxymethyl-4-trimethylsilyloxycyclohexylcarboxylate; methyl 1-methoxymethyl-cyclohexylcarboxylate; methyl 1-(3,4-dihydro-1-hydro-isobenzo-1-yl) cyclopentylcarboxylate; tert-butyl-4-hydroxy-1-(methoxymethyl) cyclohexanecarboxylate; tert-butyl-4-(tert-butyldimethylsiloxy)-1-(methoxymethyl) cyclohexanecarboxylate; tert-butyl-4-(5-aminopyridin-2-oxo)-1-(methoxymethyl) cyclohexanecarboxylate; tert-butyl-1-methoxymethyl 4-(5-nitropyridine 2-oxo) cyclohexanecarboxylate; ethyl 1-(2-methoxy-ethoxymethyl)-cyclohexanecarboxylate, ethyl-4,4-difluoro-1-(methoxymethyl)cyclohexanecarboxylate; 4-benzyloxymethyl-piperidine-1,4-dicarboxylic acid 1-tert-butyl ester-4-ethyl ester; ethyl 4-benzyloxymethyl-piperidine-4-carboxylate; ethyl 1-((benzyloxymethyl)methyl)2-oxocyclohexanecarboxylate; 2-benzyloxymethyl-2-ethoxycarbonylcyclohexanol; 2-benzyloxymethyl-2-ethoxycarbonyl-1-(tetrahydropyran-2-yl)-oxo-cyclohexane; ethyl 4-methoxymethylpiperidine-4-carboxylate; methyl 5-methoxyethyl-2-phenyl-[1.3] dioxane-5-carboxylate; ethyl 2-oxahexa-oxo-furo-[1.3]dithiahexa-2-carboxylate; diethyl-3-phenyl-6,6-(ethylenedioxy)-2-oxo-3-azabicyclo[3.3.1>nonane-1,5-dicarboxylate; methyl tetrahydro-(3,4-dihydro-1H-isobenzo-1-yl)-2H-pyran-4-carboxylate;
methyl tetrahydro-(3,4-dihydro-1H-isobenzo-1-yl)-2H-pyran-4-carboxylate; methyl 1-(3,4-dihydro-1H-isobenzo-1-yl)cyclohexanecarboxylate; methyl tetrahydro-3,4-dihydro-5-methyl-1H-isobenzo-1-yl)-2H-pyran-4-carboxylate; ethyl 4,4-difluoro-1-(methoxymethyl) cyclohexanecarboxylate, ethyl 2-(methoxymethyl) tetrahydro-2H-pyran-2-carboxylate; 3-methoxymethyl-3-ethoxycarbonyl-1-methyl-cyclohexene (1); methyl 2,3,3a,4,5,7a-hexahydro-3,3a-dimethyl-1,5-di-(2-trimethylsilylethoxy-oxo)inden-7a-carboxylate; 1-benzyloxymethyl-1-methoxycarbonyl-2,5-cyclohexene;

Methyl 4-benzyl-7-methoxy-3-oxo-3,4-dihydro-2H-1,5-benzothia-4-carboxylate; methyl 4-benzyloxymethyl-3-(4-methoxybenzyl)-5-methyl-7-oxo-6-oxa-3-aza-bicyclo[3.2.0]heptane-4-carboxylate.

Among the compounds with the general formula (IV), examples of specific suitable compounds are listed as follows: 9-methoxymethyl-fluorene carboxylic acid-(9)-methyl ester; 9-ethoxymethyl-fluorene carboxylic acid-(9)-methyl ester; 9-methoxymethyl-fluorene carboxylic acid-(9)-ethyl ester; 9-methoxymethyl-fluorene carboxylic acid-(9)-n-butyl ester; 9-methoxymethyl-fluorene carboxylic acid-(9)-isobutyl ester; 9-methoxymethyl-fluorene carboxylic acid-(9)-isopropyl ester; 9-ethoxymethyl-fluorene carboxylic acid-(9)-ethyl ester; 9-ethoxymethyl-fluorene carboxylic acid-(9)-n-butyl ester; 9-ethoxymethyl-fluorene carboxylic acid-(9)-isobutyl ester; 9-ethoxymethyl-fluorene carboxylic acid-(9)-isopropyl ester; Bis <9-methoxycarbonyl-fluoren-9-yl>-diethyl ether; 1,2,3,4,5-penta(methoxycarbonyl)-5-(methoxymethyl) cyclopentadiene.

Another preferred compound of the electron donor compound of the present invention is an unsaturated ring-substituted diacid ester compound selected from the compounds represented by the general formula (V):

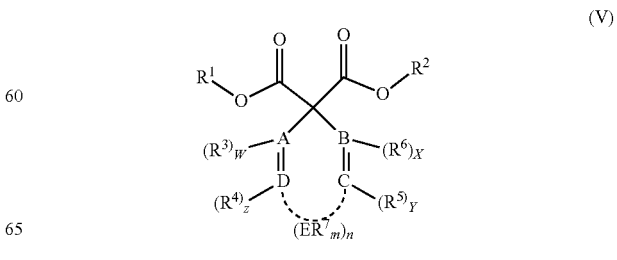

Wherein A, B, C, D and E are each selected from carbon atoms or heteroatoms selected from N, O and S; W, X, Y, Z and m are 0 or 1;

When n is equal to 0:
I) A, B, C and D are each carbon atoms, X, Y, Z and W are 1; or
II) A is a nitrogen atom, B, C and D are each carbon atoms, W is 0, X, Y and Z are 1; or
III) A and D are nitrogen atoms, B and C are carbon atoms, W and Z are 0, X and Y are 1; or
IV) D is a nitrogen atom, A, B and C are each carbon atoms, Z is 0, W, X and Y are 1; or When n is equal to 1:
i) A, B, C, D and E are each carbon atoms, m is 2, W, X, Y and Z are 1; or
ii) E is a nitrogen atom, A, B, C and D are each carbon atoms, m is 1, W, X, Y and Z are 1; or
iii) E is an oxygen atom, A, B, C and D are each carbon atoms, m is 0, W, X, Y and Z are 1; or
iv) E is a sulfur atom, A, B, C and D are each carbon atoms, m is 0, W, X, Y and Z are 1; or
v) D and E are nitrogen atoms, A, B and C are each carbon atoms, m is 1, W, X and Y are 1 and Z is 0.

$R^1$ and $R^2$ are same or different $C_1$-$C_{20}$ hydrocarbon groups, such as $C_1$-$C_{20}$ linear or branched alkyl, alkenyl, $C_3$-$C_{20}$ cycloalkyl, $C_6$-$C_{20}$ aryl, $C_7$-$C_{20}$ alkaryl and $C_7$-$C_{20}$ aralkyl group; $R^3$-$R^7$ are same or different, and are each selected from a hydrogen atom, halogen atom, oxygen atom, sulfur atom and $C_1$-$C_{20}$ hydrocarbon group, such as $C_1$-$C_{20}$ linear or branched alkyl, $C_3$-$C_{20}$ cycloalkyl, $C_6$-$C_{20}$ aryl, $C_7$-$C_{20}$ alkaryl and $C_7$-$C_{20}$ aralkyl group;

Said $R^1$-$R^7$ each may optionally contain one or more R atoms as a substituent of a carbon atom or hydrogen atom, or both, where R is a heteroatom, a linear or branched $C_1$-$C_{20}$ alkyl, $C_3$-$C_{20}$ cycloalkyl, $C_6$-$C_{20}$aryl, $C_7$-$C_{20}$ alkaryl and $C_7$-$C_{20}$ aralkyl group; wherein any two groups of $R^1$-$R^7$ may be bonded to each other to generate one or more spiro ring or fused ring structures.

The examples of the compounds included in the general formula (V) are listed as follows:
diethyl 3,5-diphenyl 2H pyrrole-2,2-dicarboxylate; diethyl 3-(3-chlorophenyl)-5-methyl-pyrrole-2,2-dicarboxylate; diethyl 3-(3-bromophenyl)-5-methyl-pyrrole-2,2-dicarboxylate; diethyl-3-(p-chlorobenzene)-5-phenyl-2H-pyrrole-2,2-dicarboxylate; dimethyl fluorene-9,9-dicarboxylate; diethyl fluorene-9,9-dicarboxylate; di-n-propyl fluorene-9,9-dicarboxylate; di-isopropyl di-n-butyl fluorene-9,9-dicarboxylate; diisobutyl fluorene-9,9-dicarboxylate; di-n-pentyl fluorene-9,9-dicarboxylate; di-n-hexyl fluorene-9,9-dicarboxylate; di-n-heptyl fluorene-9,9-dicarboxylate; di-n-octyl fluorene-9,9-dicarboxylate; dibenzyl fluorene-9,9-dicarboxylate; dihexadecyl fluorene-9,9-dicarboxylate; dibenzyl fluorene-9,9-dicarboxylate; dipropenyl fluorene-9,9-dicarboxylate; 9-methyl carboxylate-9-ethyl carboxylate-fluorene; 9-methyl carboxylate-9-n-propyl carboxylate-fluorene; 9-methyl carboxylate-9-isopropyl carboxylate-fluorene; 9-methyl carboxylate-9-n-butyl carboxylate-fluorene; 9-methyl carboxylate-9-isobutyl carboxylate-fluorene; dimethyl-4H-benzo<g>thio<2,3-e>indazole-4,4-dicarboxylate; diethyl-5-phenyl-3(p-toluene)-2H-pyrrole-2,2-dicarboxylate; diethyl-3(p-methoxybenzene)-5-phenyl-2H-pyrrole-2,2-dicarboxylate; diethyl 5-(p-nitro)-3-phenyl-2H-pyrrole-2,2-dicarboxylate; diethyl-2,3-diphenyl-H-indene-1,1-dicarboxylate; diethyl-2-phenyl-1H-indene-1,1-dicarboxylate; diethyl-2-(4-chlorobenzene)-1H-indene-1,1-dicarboxylate; diethyl-2-(4-methoxyphenyl)-1H-indene-1,1-dicarboxylate; dimethyl 3-(4-methylbenzene)-2-phenyl-1H-indene-1,1-dicarboxylate; dimethyl-3-(4-nitrobenzene)-1H-indene-1,1-dicarboxylate; dimethyl amino-4-pentamethoxycarbonyl-1,2,3,5,5-pentamethoxycarbonylcyclopentadiene; 3-phenyl-indene-1,1-dicarboxylate; dimethyl-5-(p-chlorobenzene) 3-phenyl-2H-pyrrole-2,2-dicarboxylate; dimethyl 3-(p-nitrobenzene)-5-phenyl-2H-pyrrole-dicarboxylate; dimethyl 3-(m-nitrobenzene)-5-phenyl-2H-pyrrole-2,2-dicarboxylate; dimethyl 5-(m-nitrobenzene) 5-phenyl-2H-pyrrole-2,2-dicarboxylate; dimethyl 5,6-dimethyl-5H, 6H-cyclopentadien-indole-11,11-dicarboxylate; 1-(2-nitrophenylthio)-2,3,4,5,5-methyl carboxylate-cyclopentadiene; 1-(2,4-dinitrobenzene)-2,3,4,5,5-methyl pentacarboxylate-cyclopentadiene; methyl-2-tert-butyl-3-methyl-1H-indene-1,1-dicarboxylate; dimethyl 3-methyl-2-trimethylsilyl-indene-1,1-dicarboxylate; dimethyl 3-methyl-2-phenyl-indene-1,1-dicarboxylate; diethyl-2,3-di-n-propyl-1H-indene-1,1-dicarboxylate; dimethyl-3-hydroxymethyl-2-phenyl-1H-indene-1,1-dicarboxylate; dimethyl-2-tert-butyl-5,6-dimethoxy-3-methyl-1H-indene-1,1-dicarboxylate; dimethyl-2-phenyl-3-(thia-2-yl) 1H-indene-1,1-dicarboxylate; dimethyl-3-(2-methylbenzene)2-phenyl-H-indene-1,1-dicarboxylate; dimethyl 3-(2-methoxycarbonylphenyl)-2-phenyl-1H-indene-1,1-dicarboxylate; dimethyl 3-(4-trifluoromethylbenzene) 2-phenyl-H-indene-1,1-dicarboxylate; dimethyl 3-(4-acetylbenzene) 2-phenyl-1H-indene-1,1-dicarboxylate; dimethyl-2-(2-cyclohex-1-ene)-3-(4-acetylbenzene)-1H-indene-1,1-dicarboxylate; dimethyl 2-[(ethoxycarbonyl)methyl]-1H-indene-1,1-dicarboxylate; 1,1-diethyl-H-indene-1,1-dicarboxylate; ethyl 7-chloro-5methyl-pyrazolo[4,3-d]pyrimidine-3,3-dicarboxylate; ethyl 5-amino-7-methyl-pyrazolo[4,3-d]pyrimidine-3,3-dicarboxylate; ethyl 7-methoxy-5-methyl-pyrazolo[4,3-d]pyrimidine-3,3-dicarboxylate; 1-p-tolylamino-2,3,4,5,5-pentamethoxycarbonylcyclopentadiene; dimethyl-3H-phenanthro<9,10-c>pyrazole-3,3-dicarboxylate; 3,3-bis(methoxycarbonyl)-3H-indazole; 3,3-bis(ethoxycarbonyl) 3H-indazole; 1-trichloromethyl-1,3,5,5-pentamethoxycarbonylcyclopentadiene; 1-(2-methyl-4-nitrobenzene)-pentamethoxycarbonylcyclopentadiene; 1-(2-iodo-4-nitrobenzene)-pentamethoxycarbonylcyclopentadiene; 2-(2-iodo-4-nitrobenzene)-1,3,4,5,5-pentamethoxycarbonylcyclopentadiene; 1-(2,4-dinitrobenzene)-2,3,4,5,5-pentamethoxycarbonylcyclopentadiene; 4-benzyl-1,2,3,5,5-penta(methoxycarbonyl)cyclopentadiene; 3-benzyl-1,2,4,5,5-penta (methoxycarbonyl)cyclopentadiene; 2-(trifluoromethyl)-5-carbonyl-3,3-bis (methoxycarbonyl)-3H-indole; 2-(trifluoromethyl)-5-carbonyl-7-methyl-3,3-bis (methoxycarbonyl)-3H-indole; 3-(trifluoromethyl)-5-hydroxy-7-methoxy-3,3-bis (methoxycarbonyl)-3H-indole; diethyl-3-phenyl-5(p-toluene) 2H-pyrrole-2,2-dicarboxylate; diethyl-2-(4-chlorobenzene)-5-morpholine-4H-imidazole-4,4-dicarboxylate; 4,5,5-methyl tricarboxylate-1,2,3-trichlorocyclopentadiene; methyl-3-methyl-4-trimethylsilyl-cyclopenta-2,4-diene-1,1-dicarboxylate; diethyl-2,5-diphenyl-4H-imidazole-4,4-dicarboxylate; diethyl-3-benzyl-2-phenyl-1H-indene-1,1-dicarboxylate; diethyl-3-(4-(methoxycarbonyl)phenyl) 2-phenyl-1H-indene-1,1-dicarboxylate; diethyl-3-(4-acetylbenzene) 2-phenyl-1H-indene-1,1-dicarboxylate; diethyl-2-methoxymethyl-1H-indene-1,1-dicarboxylate; diethyl-2-tert-butyl-1H-indene-1,1-dicarboxylate; dimethyl 2-n-butyl-1H-indene-1,1-dicarboxylate; diethyl 2-n-butyl-1H-indene-1,1-dicarboxylate; diethyl 2-n-hexyl-1H-indene-1,1-dicarboxylate; diethyl-2-(3-cyano-1-propyl)-1H-indene-1,1- dicarboxylate; diethyl-2-diethoxymethyl-1H-indene-1,1-dicarboxylate; diethyl-2-(4-methoxyphenyl)-1H-indene-1,1-dicarboxylate; diethyl-2-(1-cyclohexene)-1H-indene-1,1-dicarboxylate; diethyl-2-(1-cyclohexyl)-H-indene-1,1-dicarboxylate; diethyl-3-(3-toluene)-2-phenyl-1H-indene-1,1-dicarboxylate; diethyl-3-(3-nitrobenzene)-2-phenyl-1H-indene-1,1-dicarboxylate; diethyl 13H-indeno[1,2-e]phenanthrene-13,13-dicarboxylate; diethyl-2-hexyl-3-(4-methoxyphenyl) 1H-indene-1,1-dicarboxylate; ethyl cyclopenta[c]thia-5,5-dicarboxylate; 4-[4-[4-(methylsulfonic acid)benzene]1,1-bis (methyloxy)cyclopenta-2,4-dien-3-yl]pyridine; fluorene-4,9,9-dicarboxylic acid-4-tert-butyl-9,9-dicarboxylate; 4-(4-amino-pyridin-3-ylcarbamoyl)-fluoren-9,9-dicarboxylate; 4-(3-amino-pyridin-4-ylcarbamoyl)-fluoren-9,9-dicarboxylate; diethyl-3-iodo-2-phenyl-H-indene-1,1-dicarboxylate; diethyl-3-iodo-2-n-pentyl-1H-indene-1,1-dicarboxylate; diethyl-3-iodo-2-(3-methoxyphenyl)-1H-indene-1,1-dicarboxylate; diethyl-3-iodo-2-(naphthalen-2-yl)-1H-indene-1,1-dicarboxylate; di-n-hexyl-fluorene-9,9-dicarboxylate; di-n-heptyl-fluorene-9,9-dicarboxylate; diethyl-2-benzene-3H-indene-3,3-dicarboxylate; diethyl-2-bromo-1H-indene-1,1-dicarboxylate;

1-ethyl-1-methyl-cyclohexa-2,5-diene-1,1-dicarboxylate; N, 4,4-triethoxycarbonyl-1,4-dihydro-pyridine; 2,6-diphenyl-4,4-dimethoxycarbonyl-4H-pyrane; 2,6-diphenyl-4,4-dimethoxycarbonyl-1,4-dihydropyridine; 2,6-bis(4-chlorobenzene)-4,4-dimethoxycarbonyl-4H-pyrane; 2,6-bis(4-methoxyphenyl)-4,4-dimethoxycarbonyl-4H-pyrane; 2,6-bis(4-chlorobenzene)-4,4-dimethoxycarbonyl-1,4-dihydropyridine; 2,6-bis(4-methoxyphenyl)-4,4-dimethoxycarbonyl-1,4-dihydropyridine; 1-cyclopentyl-4,4-bis(methoxycarbonyl)-1,4-dihydropyridine; 1-n-hexyl-4,4-bis(methoxycarbonyl)-1,4-dihydropyridine; 1-methoxy-6,6-dicarboxyloxyloxymethyl-cyclohexa-1,4-diene; dimethyl 1,4-dihydronaphthalene-1,1-dicarboxylate; 2,6-bis(4-chlorobenzene)-4,4-dimethoxycarbonyl-4H-thiopyrane; diethyl-3-bromo-1,4-dihydro-1-methylpyridazino[3,4-b]quinoxaline-4,4-dicarboxylate; diethyl-5-bromo-3-phenyl-1,4-dihydropyridazine-4,4-dicarboxylate; trihexyl-3-phenyl-1,4-dihydropyridazine-4,4,5-tricarboxylate; 1-phenylethyl-bis (methoxycarbonyl) 1,4-dihydropyridine; diethyl-2-methyl-6-benzene(4H-pyran) 4,4-dicarboxylate; 1-(2-naphthylmethyl)-4,4-bis(methoxycarbonyl)-1,4-dihydropyridine; dimethyl-3-acetyl-1-methylquinoline-4,4 (1H)-dicarboxylate.

Examples of suitable specific compounds with the general formula (V) in the electron donor compounds of the present invention are: dimethyl fluorene-9,9-dicarboxylate; diethyl fluorene-9,9-dicarboxylate; di-n-propyl fluorene-9,9-dicarboxylate; diisopropyl fluorene-9,9-dicarboxylate; di-n-butyl fluorene-9,9-dicarboxylate; diisobutyl fluorene-9,9-dicarboxylate; di-n-pentyl fluorene-9,9-dicarboxylate; di-n-hexyl fluorene-9,9-dicarboxylate; di-n-heptyl fluorene-9,9-dicarboxylate; di-n-octyl fluorene-9,9-dicarboxylate; diphenyl fluorene-9,9-dicarboxylate; dihexadecyl fluorene-9,9-dicarboxylate; dibenzyl fluorene-9,9-dicarboxylate; dipropenyl fluorene-9,9-dicarboxylate; 9-methyl carboxylate-9-ethyl carboxylate-fluorene; 9-methyl carboxylate-9-n-propyl carboxylate-fluorene; 9-methyl carboxylate-9-isopropyl carboxylate-fluorene; 9-methyl carboxylate-9-n-butyl carboxylate-fluorene; 9-methyl carboxylate-9-isobutyl carboxylate-fluorene; 9-ethyl carboxylate-9-n-propyl carboxylate-fluorene; 9-ethyl carboxylate-9-isopropyl carboxylate-fluorene; 9-ethyl carboxylate-9-n-butyl carboxylate-fluorene; 9-ethyl carboxylate-9-isobutyl carboxylate-fluorene.

The present invention also provides a method for preparing the olefin polymerization solid catalyst component by contacting the olefin polymerization catalyst carrier with a titanium compound and an electron donor compound to obtain a solid catalyst component.

The specific preparation method comprises the following steps: firstly, an olefin polymerization catalyst carrier of the invention is contacted with a titanium compound and then is reacted with an electron donor compound for 1 to 3 hours; after the reaction, the solid product is treated with a solution of a titanium compound or with a mixture of an inert organic solvent and a titanium compound for 1 to 4 times, the solid is washed with an inert organic solvent for 1 to 7 times and then dried to obtain a solid catalyst component.

Preferably, the inert organic solvent (E) and the olefin polymerization catalyst carrier are formulated into a suspension, then contacted with the titanium compound and reacted with the electron donor compound for 1 to 3 hours. When the suspension is formulated, the titanium compound is contacted with the suspension, where the suspension may be added to the titanium compound or the titanium compound may be added to the suspension, the addition may be either rapid or slow/dropwise. The contact temperature is −30° C. to 150° C., preferably −15° C. to 80° C. The contact temperature of the electron donor compound with the suspension and the titanium compound is 0° C. to 150° C., preferably 20° C. to 100° C. The molar ratio of the inert organic solvent to the titanium compound is from 0 to 100, preferably from 0.5 to 40. The treatment temperature is from 0° C. to 150° C., preferably from 80° C. to 120° C. The solid is washed with an inert organic solvent for 1 to 7 times and then dried to obtain a solid catalyst component. The temperature is 0° C. to 150° C., preferably 20° C. to 100° C. for the first washing with the inert organic solvent, and the second washing temperature is 0° C. to 150° C., preferably 40° C. to 80° C.

The present invention is to provide a catalyst for olefin $CH_2$=CHR polymerization, wherein R is hydrogen or a hydrocarbon group having 1-12 carbon atoms, the catalyst comprising the reaction product of the following materials:

a) an olefin polymerization solid catalyst component of the present invention;

b) at least one organic aluminum compound of the general formula $AlR_nX_{(3-n)}$, wherein R is hydrogen, hydrocarbon group having 1-20 carbon atoms; X is halogen, n is an integer of $0 \leq n \leq 3$; and optionally, c) at least one external electron donor compound.

Preferably, the organoaluminum compound (b) is selected from the group consisting of trialkylaluminum compound such as trimethylaluminum, triethylaluminum, triisobutylaluminum, tri-n-butyl aluminum, tri-n-hexyl aluminum, tri-octyl aluminum. It is also possible to use trialkylaluminum and alkylaluminum halide, or a mixture of alkylaluminum sesquichloride such as $AlEt_2Cl$ and $Al_2Et_3Cl_3$; alkylaluminoxanes can also be used.

For applications where good isotacticity is required, an external electron donor compound can be used. The external electron donor is selected from siloxane compounds represented by general formula $R_nSi(OR_1)_{4-n}$, wherein R and $R_1$ are $C_1$-$C_{18}$ hydrocarbon group, which may optionally be substituted by heteroatoms; n is an integer of $0 \leq n \leq 3$.

Said specific silane compounds may be: trimethylmethoxysilane, trimethylethoxysilane, tri-n-propylhnethoxysilane, tri-n-propylethoxysilane, tri-n-butylmethoxysilane, triisobutylethoxysilane, trihexylmethylsilane, trihexylethoxysilane, dimethyldimethoxysilane, dimethyldiethoxysilane, di-n-propyldimethoxysilane, diisopropyldimethoxysilane, di-n-propyldiethoxysilane, diisopropyldiethoxysilane, di-n-butyldiethoxysilane, diisobutyldiethoxysilane, di-tert-butyldimethoxysilane, di-tert-butyldiethoxysilane, di-n-butyldimethoxysilane, diisobutyldimethoxysilane, di-tert-butyldiethoxysilane, di-n-butyldiethoxysilane, n-butylmethyldimethoxysilane, di(2-ethylhexyl)dimethoxysilane, di(2-ethylhexyl)diethoxysilane, dicyclohexyldimethoxysilane, dicyclohexyldiethoxysilane, dicyclopentyldimethoxysilane, dicyclopentyldiethoxysilane, cyclohexylmethyldimethoxysilane, cyclohexylmethyldiethoxysilane, cyclohexylethyldimethoxysilane, cyclohexylisopropyldimethoxysilane, cyclohexylethyldiethoxysilane, cyclopentylmethyldimethoxysilane, cyclopentylethyldiethoxysilane, cyclopentylisopropyldiethoxysilane, cyclopentylisobutyldimethoxysilane, cyclohexyln-propyldimethoxysilane, cyclohexyln-propyldiethoxysilane, cyclohexyln-butyldiethoxysilane, pentylmethyldimethoxysilane, pentylmethyldiethoxysilane, pentylethyldimethoxysilane, pentylethyldiethoxysilane, cyclohexyldimethylmethoxysilane, cyclohexyldiethylmethoxysilane, cyclohexyldiethylmethoxysilane, cyclohexyldiethylethoxysilane, 2-ethylhexyltrimethoxysilane, cyclohexyldimethoxysilane, cyclohexyldiethoxysilane, 2-ethylhexyltriethoxysilane, ethyltrimethoxysilane, ethyltriethoxysilane, n-propyltrimethoxysilane, n-propyltriethoxysilane, isopropyltrimethoxysilane, isopropyltriethoxysilane, n-butyltrimethoxysilane, isobutyltrimethoxysilane, tert-butyltrimethoxysilane, n-butyltriethoxysilane, cyclohexyltrimethoxysilane, cyclohexyltriethoxysilane, cyclopentyltrimethoxysilane, cyclopentyltriethoxysilane, vinyltrimethoxysilane, vinyltriethoxysilane, 2-ethylhexyltrimethoxysilane, 2-ethylhexyltriethoxysilane, pentyltrimethoxysilane, pentyltriethoxysilane, tetramethoxysilane, tetraethoxysilane, cyclohexylcyclopentyldimethoxysilane, cyclohexylcyclopentyldiethoxysilane, cyclohexylcyclopentyldipropoxysilane, 3-methylcyclohexylcyclopentyldimethoxysilane, 4-methylcyclohexylcyclopentyldimethoxysilane, 3,5-dimethylcyclohexylcyclopentyldimethoxysilane, 3-methylcyclohexylcyclohexyldimethoxysilane, di(3-methylcyclohexyl) dimethoxysilane, 4-methylcyclohexylcyclohexyldimethoxysilane, di(4-methylcyclohexyl)dimethoxysilane, 3,5-dimethylcyclohexylcyclohexyldimethoxysilane, di(3,5-dimethylcyclohexyl)dimethoxysilane, tetrapropoxysilane, tetrabutoxysilan.

The preferable compound among these organosilicon compounds are: di-n-propyldimethoxysilane, diisopropyldimethoxysilane, di-n-butyldimethoxysilane, diisobutyldimethoxysilane, di-tert-butyldimethoxysilane, di-n-butyldiethoxysilane, tert-butyltrimethoxysilane, dicyclohexyldimethoxysilane, dicyclohexyldiethoxysilane, cyclohexylmethyldimethoxysilane, cyclohexylethyldiethoxysilane, cyclohexylethyldimethoxysilane, cyclohexylethyldiethoxysilane, cyclopentylmethyldimethoxysilane, cyclopentylmethyldiethoxysilane, cyclopentylethyldimethoxysilane, cyclohexylcyclopentyldimethoxysilane, cyclohexylcyclopentyldiethoxysilane, 3-methylcyclohexylcyclopentyldimethoxysilane, 4-methylcyclohexylcyclopentyldimethoxysilane and 3,5-dimethylcyclopentyldimethoxysilane, etc. These compounds C can be used alone or in combination.

Preferred examples of silane compounds are cyclohexylmethyl dimethoxysilane; diisopropyl dimethoxysilane; di-n-butyl dimethoxysilane; diisobutyl dimethoxysilane; diphenyl dimethoxysilane; phenyltriethoxysilane; methyl tert-butyl dimethoxysilane; dicyclopentyl dimethoxysilane; 2-ethylpiperidin-2-t-butyl-dimethoxysilane and (1,1,1-trifluoro-2-propyl)-2-ethylpiperidine dimethoxysilane and (1,1,1-trifluoro-2-propyl)-methyldimethoxysilane, cyclohexyl trimethoxysilane; tert-butyl trimethoxysilane and tert-hexyl trimethoxysilane.

In order to use the catalysts of the present invention for olefin polymerization, the catalyst prepared by component a, b, c can be used for both homo-polymerization and co-polymerization. Typically, the molar ratio of component b to component a is 1-1000 mol per mol of titanium atom contained in the component a, preferably 50-800 mol per mol of titanium atom contained in the component a; and the molar ratio of component c to component a is 0.002-10, preferably 0.01-2, more preferably 0.01-0.5.

The order of the components can be added in any order. Preferably, component b is firstly added to the polymerization system, and then component c, and component a is added last.

The polymerization process of the present invention can be carried out in the presence or absence of a solvent. Olefin monomers may be gaseous or liquid phase. Hydrogen can be further added as a molecular weight modifier. Of course, the polymerization can also be carried out in the absence of molecular weight modifier. The polymerization temperature should not be greater than 200° C., preferably is between 20-100° C., and more preferably between 40-80° C. The polymerization pressure should not be more than 10 MPa, and is preferably between 1-5 MPa. Both continuous polymerization and batch polymerization process can be used. The polymerization reaction can be done in one step or divided into two or more stages.

The olefins to be homopolymerized or copolymerized using the catalyst of the present invention include linear olefins (such as: ethylene, propylene, 1-butene, 1-pentene, 1-hexene, 1-heptene, 1-nonene, 1-decene, 1-octene); branched olefins (such as: 3-methyl-1-butene and 4-methyl-1-pentene); dienes (such as: butadiene, vinyl cyclopentene and vinyl cyclohexene). The catalyst of the present invention is preferably used for polymerization of polyethylene and polypropylene. These olefins may be used alone or in combination.

In terms of the olefin polymerization conducted by using the catalyst component a, b, c of the present invention (hereinafter referred to as the main polymerization), prepolymerization is recommended to increase the activity of the catalysts as well as the isotacticity, particle properties and of the productpolymers. The prepolymerization can also be used for styrene homopolymerization.

In the prepolymerization process, the addition order of each component and monomer is arbitrary. Preferably the component b is firstly added to the system containing an inert gas or olefins to be polymerized, and then one or more olefins to be polymerized are added after addition of component a. In the process of olefin prepolymerization using organosilane, it is recommended that component b is added to the polymerization system of an inert gas or olefins to be polymerized, followed by the addition of component c, which is then followed by the addition of component a, and the olefins are added last.

The olefin polymerization catalyst carrier and the solid catalyst component of the present invention have the following advantages:
1) The carrier of the present invention has a specific chemical composition and physical properties, and can be obtained by reacting alcohol and magnesium in the presence of halogen. In particular, the carrier obtained by treating the reaction product of the alcohol and magnesium-alkoxymagnesium solid (D) under high temperature and high pressure is converted from a spherical solid having a loose and roughened surface to a cube-like shape with a smooth surface. The carrier is then reacted with a titanium compound to obtain a solid catalyst component which may contain at least one electron donor compound.

2) The size and morphology of the carrier of the invention can be adjusted by changing the temperature and pressure of the treatment. The particle size of the carrier after high temperature and high pressure treatment can be significantly smaller than that before treatment, the structure is more compact and the mechanical strength is better, In the course of operation, the carrier can maintain its basic shape without hindering the polymer chain growth, so that the catalyst particles is not broken in the effect of polymer chain growth.

3) In the present invention, the distribution of the carrier particles after high temperature and high pressure treatment is narrower, the content of the fine powder is small, the stacking density is high, and since the catalyst and the polymer replicate the structure and morphology of the carrier, the direct result is that the particle size distribution of the solid catalyst component, the catalyst and the polymer is concentrated, the content of the fine powder is small and the stacking density is high.

4) The olefin polymerization catalyst prepared by the carrier and the solid catalyst component has high activity, which is clearly higher than the activity of the catalyst prepared by the carrier of the prior technology. In particular, the carrier which is subjected to high temperature and high pressure treatment has an activity 10% greater than that of the catalyst prepared without high temperature and pressure, and can be generally 20% greater than the activity of the catalyst prepared by the prior art carriers.

5) When using the olefin polymerization catalyst prepared by the carrier, the obtained polymer has a regular morphology, a compact structure and a high stacking density.

BRIEF DESCRIPTION OF THE DRAWINGS

FIG. 1 shows XRD (X-ray diffraction) patterns of various catalyst carriers of the present invention.

DETAILED DESCRIPTION OF EMBODIMENTS

Hereinafter, the present invention will be described in detail by way of examples, but the present invention is not limited thereto.

The operation of preparing the catalyst in the examples was carried out under high purity nitrogen protection.

Example 1

In a four-necked flask equipped with a stirrer, a reflux condenser was installed and a cumulative gas meter was connected to the reflux condenser. After the whole reaction apparatus was fully purged with nitrogen, 50 mL of anhydrous oxygen free ethanol and 0.55 g of iodine were added to the vessel and dissolved, 6 g of metallic magnesium was added thereto, and the temperature was raised to the reflux temperature of ethanol under stirring. 90 mL of anhydrous ethanol and 9 g of magnesium powder were added every 10 minutes from the start of reflux, for three times in total. The viscosity of the liquid began to rise sharply at about 1-2 hours after the completion of the third addition (at this time, the reaction rate was about 85% as determined by the amount of hydrogen produced). Then, 150 mL of ethanol was added to the reaction system, the reaction continued until no hydrogen was produced. The reaction time was about 6 hours, and a suspension containing a white solid powder was obtained. The suspension was added to an autoclave, stirred at 145° C. and 1.4 MPa for 3 hours, and then filtered under pressure and dried to obtain a carrier $Mg(OEt)_2$.

Example 2

The preparation steps of the carrier were the same as those of Example 1 except that the reaction temperature in the autoclave was changed from 145° C. to 140° C., the reaction pressure was changed from 1.4 MPa to 1.0 MPa, and the carrier $Mg(OEt)_2$ was obtained after 2 hours of reaction time.

Example 3

To an autoclave fully purged with nitrogen, 40 mL of anhydrous oxygen free ethanol and 0.33 g of iodine were added and dissolved. 3 g of metallic magnesium was added thereto, and the temperature was raised to the reflux temperature of ethanol under stirring. 40 mL of anhydrous ethanol and 6 g of magnesium powder were added every 10 minutes from the start of reflux, for three times in total. The viscosity of the liquid began to rise sharply at about 1-2 hours after the completion of the third addition (at this time the reaction rate was about 85% as determined by the amount of hydrogen produced), then 80 mL of ethanol was added to the reaction system, the reaction continued until no hydrogen was produced. The entire reaction time was about 6 hour. After completion of the reaction, the mixture was heated at 140° C. and 0.8 MPa for 3 hours, and then filtered under pressure and dried to obtain a carrier Mg(OEt)2.

Example 4 Catalyst Component

To a 500 ml of fully nitrogen-purged five-necked flask equipped with a stirrer were added 10 g of carrier prepared in the Example 1 and 80 mL toluene to prepare a suspension, and then 20 mL of titanium tetrachloride was added dropwise at −15° C., after addition was completed the system was slowly warmed to 10° C., and was added 60 mL of titanium tetrachloride dropwise, then the system temperature was slowly raised to 80° C. and then, 12 mmol of dibutyl phthalate was added, and then the temperature of the system was raised up to 120° C. and maintained constant for 2 hours, then the liquid was cleaned by filter pressing and filtered, the resulting solid was washed 3 times with 120 mL titanium tetrachloride at 125° C. The resulting solid was washed two times at 60° C. and two times at room temperature with 150 mL of hexane; after removal of the liquid by filtration and drying the solid, solid powder, i.e. solid catalyst component, was obtained. Analytical results of the solid showed that the titanium content was 2.83 (wt) %, dibutyl phthalate content was 11.24 (wt) %.

Example 5

The catalyst component was prepared in the same manner as in Example 4 except that di-n-butyl phthalate was changed to 9,9-methoxymethyl fluorene.

Example 6

The catalyst component was prepared in the same manner as in Example 4 except that di-n-butyl phthalate was changed to 2-isopropyl-2-isopentyl-1,3-dimethoxypropane.

Example 7

The catalyst component was prepared in the same manner as in Example 4 except that the carrier prepared in Example 1 was replaced with the carrier prepared in Example 2.

Example 8

The catalyst component was prepared in the same manner as in Example 4 except that the carrier prepared in Example 1 was replaced with the carrier prepared in Example 2 and di-n-butyl phthalate was changed to 9,9-methoxymethyl fluorene.

Example 9

The catalyst component was prepared in the same manner as in Example 4 except that the carrier prepared in Example 1 was changed to the carrier prepared in Example 2 and the di-n-butyl phthalate was changed to 2-isopropyl-2-Isopentyl-1,3-dimethoxypropane.

Example 10

The catalyst component was prepared in the same manner as in Example 4 except that the carrier prepared in Example 1 was replaced with the carrier prepared in Example 3.

Example 11

In a four-necked flask equipped with a stirrer, a reflux condenser was installed and a cumulative gas meter was connected to the reflux condenser. After the whole reaction apparatus was fully purged with nitrogen, 50 mL of anhydrous oxygen free ethanol and 0.55 g of iodine were added to the vessel and dissolved, 6 g of metallic magnesium was added thereto, and the temperature was raised to the reflux temperature of ethanol under stirring. 90 mL of anhydrous ethanol and 9 g of magnesium powder were added every 10 minutes from the start of reflux, for three times in total. The viscosity of the liquid began to rise sharply at about 1-2 hours after the completion of the third addition (at this time, the reaction rate was about 85% as determined by the amount of hydrogen produced). Then, 150 mL of ethanol was added to the reaction system, the reaction continued until no hydrogen was produced. The total reaction time was about 6 hours, and a suspension containing a white solid powder was obtained and then dried to obtain a white solid powder.

Example 12

The catalyst component was prepared in the same manner as in Example 4 except that the carrier prepared in Example 1 was changed to the carrier prepared in Example 11.

Example 13

The catalyst component was prepared in the same manner as in Example 4 except that the carrier prepared in Example 1 was replaced with the carrier prepared in Example 11 and di-n-butyl phthalate was changed to 9,9-methoxymethyl fluorene.

Example 14

The catalyst component was prepared in the same manner as in Example 4 except that the carrier prepared in Example 1 was changed to the carrier prepared in Example 11 and the di-n-butyl phthalate was changed to 2-isopropyl-2-isopentyl-1,3-dimethoxypropane.

Example 15

The catalyst component was prepared in the same manner as in Example 4 except that di-n-butyl phthalate was changed to ethyl 2,3-diisopropylsuccinate.

Example 16

The catalyst component was prepared in the same manner as in Example 4 except that di-n-butyl phthalate was changed to 9-methoxymethyl-fluorenylcarboxylic acid-(9) ethyl ester.

Example 17

The catalyst component was prepared in the same manner as in Example 4 except that di-n-butyl phthalate was changed to diethyl fluorene-9,9-dicarboxylate.

Example 18

The catalyst component was prepared in the same manner as in Example 4 except that the carrier prepared in Example 1 was changed to the carrier prepared in Example 11 and the di-n-butyl phthalate was changed to ethyl 2,3-diisopropylsuccinate.

Example 19

The catalyst component was prepared in the same manner as in Example 4 except that the carrier prepared in Example 1 was replaced with the carrier prepared in Example 11 and the di-n-butyl phthalate was changed to 9-methoxymethyl-fluorene carboxylic acid-(9)-ethyl ester.

Example 20

The catalyst component was prepared in the same manner as in Example 4 except that the carrier prepared in Example 1 was changed to the carrier prepared in Example 11 and the di-n-butyl phthalate was changed to diethyl fluorene-9,9-dicarboxylate.

Example 21

The carrier was prepared in the same manner as the same as in Example 1 except that the alcohol was changed to a mixed alcohol of ethanol and n-butanol in a volume ratio of 5:1. The carrier $Mg(OEt)_n(O''Bu)_{2-n}$ ($0 \leq n \leq 2$) was obtained.

Example 22

The catalyst component was prepared in the same manner as in Example 4 except that the carrier of Example 1 was changed to the carrier of Example 21.

Example 23

The carrier was prepared in the same manner as in Example 1 except that the ethanol was changed to n-propanol. The carrier $Mg(O^nPr)_2$ was obtained.

Example 24

The catalyst component was prepared in the same manner as in Example 4 except that the carrier of Example 1 was changed to the carrier of Example 23.

Example 25

To an autoclave fully purged with nitrogen, 40 mL of anhydrous oxygen free ethanol and 0.33 g of iodine were added and dissolved. 3 g of metallic magnesium was added thereto, and the temperature was raised to the reflux temperature of ethanol under stirring. 40 mL of anhydrous ethanol and 6 g of magnesium powder were added every 10 minutes from the start of reflux, for three times in total. The viscosity of the liquid began to rise sharply at about 1-2 hours after the completion of the third addition (at this time the reaction rate was about 85% as determined by the amount of hydrogen produced), then 80 mL of ethanol was added to the reaction system, the reaction continued until no hydrogen was produced. The entire reaction time was about 6 hour. After completion of the reaction, the mixture was heated at 160° C. and 2 MPa for 1 hours, and then filtered under pressure and dried to obtain a carrier Mg(OEt)2.

Example 26

The catalyst component was prepared in the same manner as in Example 4 except that the carrier prepared in Example 1 was changed to the carrier prepared in Example 25.

Example 27

The catalyst component was prepared in the same manner as in Example 4 except that the carrier prepared in Example 1 was changed to the carrier prepared in Example 25 and the di-n-butyl phthalate was changed to 9,9-methoxymethylfluorene.

Example 28

The catalyst component was prepared in the same manner as in Example 4 except that the carrier prepared in Example 1 was changed to the carrier prepared in Example 25 and the di-n-butyl phthalate was changed to 2-isopropyl-2-isopentyl-1,3-dimethoxypropane.

Example 29

The catalyst component was prepared in the same manner as in Example 4 except that the carrier prepared in Example 1 was changed to the carrier prepared in Example 25 and the di-n-butyl phthalate was changed to ethyl 2,3-diisopropylsuccinate.

Example 30

The catalyst component was prepared in the same manner as in Example 4 except that the carrier prepared in Example 1 was replaced with the carrier prepared in Example 25 and the di-n-butyl phthalate was changed to 9-methoxymethyl-fluorenylcarboxylic acid-(9)-ethyl ester.

Example 31

The catalyst component was prepared in the same manner as in Example 4 except that the carrier prepared in Example 1 was replaced with the carrier prepared in Example 25 and the di-n-butyl phthalate was changed to diethyl fluorene-9,9-dicarboxylate.

Example 32

To an autoclave fully purged with nitrogen, 40 mL of anhydrous oxygen free ethanol and 0.33 g of iodine were added and dissolved. 3 g of metallic magnesium was added thereto, and the temperature was raised to the reflux temperature of ethanol under stirring. 40 mL of anhydrous ethanol and 6 g of magnesium powder were added every 10 minutes from the start of reflux, for three times in total. The viscosity of the liquid began to rise sharply at about 1-2 hours after the completion of the third addition (at this time the reaction rate was about 85% as determined by the amount of hydrogen produced), then 80 mL of ethanol was added to the reaction system, the reaction continued until no hydrogen was produced. The entire reaction time was about 6 hour. After completion of the reaction, the mixture was heated at 80° C. and 2.5 MPa for 1 hours, and then filtered under pressure and dried to obtain a carrier $Mg(OEt)_2$.

Example 33

The catalyst component was prepared in the same manner as in Example 4 except that the carrier prepared in Example 1 was replaced with the carrier prepared in Example 32.

Comparative Example 1

To a 1000 mL of flask fully purged with nitrogen, 400 mL of white oil, 46 mL of anhydrous ethanol and 20 g of magnesium chloride were added, stirred and heated to 130° C. at which the reaction was continued for 3 hours. The reactant was transferred to an emulsifier for emulsification at 5000 rpm for 20 min and then transferred to 5000 mL of hexane at −20° C., stirred at low temperature for 5 hours and then washed with hexane for 3 to 6 times. The white powder was filtered, followed by removing hexane after drying to obtain a spherical carrier.

Comparative Example 2

To a 500 mL of 5-necked flask fully purged with nitrogen and equipped with a stirrer, 10 g of the spherical carrier prepared in Comparative Example 1 and 150 mL of titanium tetrachloride were added to produce a suspension, maintained at −15° C. for 1 hour, and slowly raised to 80° C., 3.5 g of di-n-butyl phthalate was added, the temperature was raised to 110° C. for 1 hour, and then the liquid was filtered off under pressure. The resulting solid was washed with 120 mL of titanium tetrachloride at 125° C. three times. The resulting solid was washed with 150 mL of hexane at 60° C. four times, followed by filtering the liquid and drying to obtain a solid powder as a solid catalyst component.

Comparative Example 3

The catalyst component was prepared in the same manner as in Comparative Example 2 except that di-n-butyl phthalate was changed to 9,9-methoxymethyl fluorene.

Comparative Example 4

The catalyst component was prepared in the same manner as in Comparative Example 2 except that di-n-butyl phthalate was changed to 2-isopropyl-2-isopentyl-1,3-dimethoxypropane.

Comparative Example 5

The carrier was prepared in the same manner as in Example 1 except that the ethanol was changed to a mixed alcohol solution of methanol, ethanol and isopropanol in a volume ratio of 1:7.5:1.5. The carrier $Mg(OMe)_x(OEt)_y(O''Pr)_z(x+y+z=2)$ was obtained.

Comparative Example 6

The catalyst was prepared in the same manner as in Example 4 except that the carrier of Example 1 was changed to the carrier of Comparative Example 5.

Comparative Example 7

The carrier was prepared in the same manner as in Example 1 except that the ethanol was changed to a mixed alcohol solution of methanol, ethanol and n-butanol in a volume ratio of 1:5:1. The carrier $Mg(OMe)_x(OEt)_y(O''Bu)_z(x+y+z=2)$ was obtained.

Comparative Example 8

The catalyst was prepared in the same manner as in Example 4 except that the carrier of Example 1 was changed to the carrier of Comparative Example 7.

As can be seen from FIG. 1, the two sets of diffraction angles 2θ of the carrier obtained in Example 1 are in the range of 10-11° and 23-25°, and there are two main diffraction peaks in each set, the corresponding diffraction angle 2θ values of the highest peaks are 10.4566° and 23.1095°.

The carrier prepared in Example 2 has the above characteristics, and the corresponding diffraction angles 2θ of the highest peaks in each set are 10.4904° and 23.1433°, respectively.

The carrier obtained in Example 11 has three diffraction peaks in the range of 5-15° of the diffraction angle 2θ, and the corresponding diffraction angle 2θ of the highest peak is 10.8660°, and there is only one shoulder peak in the range of 20-30° and no main diffraction peak.

The carrier of Comparative Example 1 is a magnesium chloride alcoholate carrier, there are two diffraction peaks in the range of 5 to 15 of 2θ, and the corresponding 2θ value of the highest peak is slightly smaller than that of the above-mentioned ethoxymagnesium carrier.

The diffraction peaks of the carrier obtained in Example 3 were tested to be characterized in that the corresponding diffraction angles 2θ of the highest peaks in each set are 10.48520 and 23.1045°, respectively.

The diffraction peaks of the obtained carrier of Example 21 are characterized in that the corresponding diffraction angles 2θ of the highest peaks in each set are 9.3805° and 21.0952°, respectively.

The diffraction peaks of the obtained carrier of Example 23 are characterized in that the corresponding diffraction angles 2θ of the highest peaks in each set are 8.9458° and 24.19830, respectively.

The diffraction peaks of the obtained carrier of Example 25 are characterized in that the corresponding diffraction angles 2θ of the highest peaks in each set are 10.4570° and 23.1842°, respectively.

The diffraction peaks of the obtained carrier of Example 32 are characterized in that the corresponding diffraction angles 2θ of the highest peak in each set are 10.4445° and 23.1350°, respectively.

Propylene Polymerization

Propylene polymerization evaluation was made by using the solid catalyst components prepared in the Examples and comparison Examples 2-4:

To a 5 L of stainless steel reactor fully purged with nitrogen were added 5 mL of solution of triethylaluminum in hexane at a concentration of 0.5 mol/L and 1 mL of solution of methyl cyclohexyl dimethoxy silane (CMMS) in hexane at a concentration of 0.1 mol/L and 10 mg of prepared catalyst, 10 mL of hexane was added to rinse the feed lines, and then 2 L of hydrogen (standard state) and 2.5 L of purified propylene were added, the reaction was controlled at 20° C. to prepolymerize for 5 minutes, the temperature was raised to 70° C., and at this temperature the polymerization reaction was carried out for 1 hour. After the reaction, the reactor was cooled and the stirring was stopped, the reaction product was discharged and dried to obtain a polymer. (Stacking density of the polymer measured by JB/T 2412-2008 method, isotacticity measured by JB/T 3682-2000 method). The polymerization activity was shown in Table 1.

TABLE 1

| | Catalyst performance | | | | | |
|---|---|---|---|---|---|---|
| Example No. | internal electron donor type | Wt % | titanium Wt % | activity Kg/gCat · h$^{-1}$ | iso-tacticity % | stacking density g/cm$^3$ |
| Example 4 | di-n-butyl phthalate | 11.24 | 2.83 | 5.4 | 98.6 | 0.41 |
| Example 5 | 9,9-methoxymethylfluorene | 15.09 | 3.69 | 6.8 | 99.1 | 0.42 |
| Example 6 | 2-isopropyl-2-isopentyl-1,3-dimethoxypropane | 16.54 | 3.17 | 6.9 | 99.1 | 0.40 |
| Example 7 | di-n-butyl phthalate | 13.10 | 3.33 | 5.2 | 98.5 | 0.40 |
| Example 8 | 9,9-methoxymethylfluorene | 20.34 | 3.19 | 6.6 | 98.9 | 0.41 |
| Example 9 | 2-isopropyl-2-isopentyl-1,3-dimethoxypropane | 10.89 | 3.14 | 6.7 | 99.3 | 0.39 |
| Example 10 | di-n-butyl phthalate | 13.14 | 3.16 | 5.0 | 98.4 | 0.41 |

TABLE 1-continued

| | Catalyst performance | | | | | |
|---|---|---|---|---|---|---|
| Example No. | internal electron donor type | Wt % | titanium Wt % | activity Kg/gCat · h$^{-1}$ | iso-tacticity % | stacking density g/cm$^3$ |
| Example 12 | di-n-butyl phthalate | 11.16 | 2.54 | 4.6 | 99.0 | 0.40 |
| Example 13 | 9,9-methoxymethylfluorene | 20.42 | 2.84 | 5.8 | 99.1 | 0.39 |
| Example 14 | 2-isopropyl-2-isopentyl-1,3-dimethoxypropane | 10.89 | 3.14 | 5.5 | 98.9 | 0.40 |
| Example 15 | ethyl 2,3-diisopropylsuccinate | 15.55 | 2.74 | 4.8 | 99.1 | 0.41 |
| Example 16 | 9-methoxymethyl-fluorenylcarboxylic acid (9)-ethyl ester | 15.80 | 3.05 | 5.5 | 98.3 | 0.42 |
| Example 17 | diethyl fluorene-9,9-dicarboxylate | 13.46 | 3.32 | 6.3 | 98.8 | 0.42 |
| Example 18 | ethyl 2,3-diisopropylsuccinate | 16.51 | 2.97 | 4.2 | 98.7 | 0.40 |
| Example 19 | 9-methoxymethyl-fluorenylcarboxylic acid (9)-ethyl ester | 16.24 | 3.64 | 5.0 | 98.2 | 0.39 |
| Example 20 | diethyl fluorene-9,9-dicarboxylate | 14.23 | 3.45 | 5.6 | 98.6 | 0.41 |
| Example 22 | di-n-butyl phthalate | 11.54 | 2.74 | 4.9 | 98.7 | 0.40 |
| Example 24 | di-n-butyl phthalate | 12.10 | 2.47 | 4.7 | 98.4 | 0.41 |
| Example 26 | di-n-butyl phthalate | 12.50 | 2.71 | 5.2 | 98.5 | 0.40 |
| Example 27 | 9,9-methoxymethylfluorene | 18.34 | 2.50 | 6.4 | 98.9 | 0.40 |
| Example 28 | 2-isopropyl-2-isopentyl-1,3-dime thoxypropane | 12.20 | 2.84 | 6.4 | 98.4 | 0.41 |
| Example 29 | ethyl 2,3-diisopropylsuccinate | 14.55 | 2.58 | 4.5 | 98.1 | 0.42 |
| Example 30 | 9-methoxymethyl-fluorenylcarboxylic acid-(9) ethyl ester | 16.24 | 3.04 | 5.6 | 98.1 | 0.39 |
| Example 31 | diethyl fluorene-9,9-dicarboxylate | 17.32 | 2.94 | 5.9 | 98.3 | 0.40 |
| Example 33 | di-n-butyl phthalate | 13.56 | 2.85 | 5.1 | 98.4 | 0.39 |
| Comparative Example 2 | di-n-butyl phthalate | 16.59 | 2.16 | 4.1 | 98.6 | 0.43 |
| Comparative Example 3 | 9,9-methoxymethylfluorene | 19.23 | 2.51 | 5.5 | 99.3 | 0.43 |
| Comparative Example 4 | 2-isopropyl-2-isopentyl-1,3-dime thoxypropane | 18.45 | 2.78 | 5.1 | 99.2 | 0.44 |
| Comparative Example 6 | di-n-butyl phthalate | 12.10 | 2.92 | 4.9 | 98.7 | 0.42 |
| Comparative Example 8 | di-n-butyl phthalate | 13.62 | 2.85 | 5.0 | 98.5 | 0.42 |

It can be seen from the polymerization results in Table 1 that the activity of the catalyst prepared by the alkoxymagnesium carrier is higher than that of the catalyst prepared by the magnesium chloride ethanol carrier. The activity centers of the catalyst prepared by the carrier of the examples obtained under high temperature and high pressure are distributed evenly, the catalyst activity is high and the polymer made using the catalyst has a higher stacking density. The propylene polymerization activity is substantially improved compared to the catalyst prepared using the carrier of the comparative example which has not been subjected to high temperature and high pressure treatment, particularly compared to the catalyst prepared by the magnesium chloride alcoholate carrier. By changing the reaction temperature, reaction pressure and reaction time of the high temperature and high pressure treatment step, the particle size and morphology of the obtained carrier particles can be adjusted to improve the performance of the catalysts.

Although the present invention has been generally described and in more detail with the specific embodiments, on the basis of the present invention, it would be obvious for those skilled in this art to make certain modifications or improvements. Therefore, these modifications or improvements made without departing from the spirit of the present invention fall in the scope of the invention as claimed.

INDUSTRIAL APPLICABILITY

The present invention relates to an olefin polymerization catalyst carrier and an olefin polymerization solid catalyst component prepared from said carrier, a titanium compound, at least one electron donor compound. For the olefin polymerization catalyst carrier of the present invention, the distribution of the carrier particles is concentrated, the content of the fine powder is small, the stacking density is high, and since the catalyst and the polymer replicate the structure and morphology of the carrier, the direct results show that the particle distribution of the solid catalyst component, the catalyst and the polymer is concentrated, the content of the fine powder is small and the stacking density is high. The olefin polymerization catalyst prepared by the carrier and the solid catalyst component has high activity, and the obtained polymer has a regular morphology, a compact structure and a high stacking density. The present invention has industrial applicability.

What is claimed is:

1. A method preparing an olefin polymerization catalyst carrier having a general formula of $Mg(OR^I)_n(OR^{II})_{2-n}$, wherein $0 \leq n \leq 2$, and $R^I$ and $R^{II}$ are same or different, and are each independently selected from a $C_1$-$C_{20}$ hydrocarbon group; and wherein in the X-ray diffraction pattern of the catalyst carrier there are a set of diffraction peaks in the range of a 2θ diffraction angle of 5°-15°, and the set of diffraction peaks contain 1-4 main diffraction peaks, the method comprising the steps of:
   (a) reacting a $C_1$-$C_{20}$ alcohol with a metal magnesium powder under the protection of nitrogen in the presence of a halogen or a halogen-containing compound to obtain a first product;
   (b) optionally drying the first product; and
   (c) subjecting the first product obtained in (a) or the dried first product obtained in (b) to a treatment pressure of from 0.2 to 5.0 MPa at a treatment temperature of from 80 to 200° C. for a duration of between 2 minutes and 6 hours, to thereby obtain the olefin polymerization catalyst carrier.

2. The method of claim 1, wherein in step (c), the treatment pressure is from 0.3 to 3.0 MPa.

3. The method of claim 2, wherein the treatment pressure is from 0.5 to 2.0 MPa.

4. The method of claim 1, wherein in step (c), the treatment temperature is from 100 to 180° C.

5. The method of claim 4, wherein the treatment temperature is from 120 to 160° C.

6. The method of claim 1, wherein the alcohol is at least one of $C_1$-$C_8$ lower alcohols.

7. The method of claim 6, wherein the alcohol is ethanol.

8. The method of claim 1, wherein the halogen in the halogen or halogen-containing compound is at least one of chlorine, bromine or iodine; and the halogen-containing compound is selected from the group consisting of $MgCl_2$, $MgBr_2$, $MgI_2$, Mg(OEt)Cl, Mg(OEt)I, $CaCl_2$), NaCl, and KBr.

9. The method of claim 8, wherein the halogen-containing compound is $MgCl_2$.

10. The method of claim 1, wherein in the catalyst carrier $Mg(OR^I)_n(OR^{II})_{2-n}$, $R^I$ and $R^{II}$ are the same or different, and are each independently selected from a $C_1$-$C_8$ hydrocarbon group.

11. The method of claim 10, wherein the $Mg(OR^I)_n(OR^{II})_{2-n}$ is dimethoxy magnesium, diethoxymagnesium, dipropoxymagnesium, dibutoxymagnesium, ethoxypropoxymagnesium or butoxyethoxymagnesium.

12. The method of claim 1, wherein in the X-ray diffraction pattern of the catalyst carrier $Mg(OR^I)_n(OR^{II})_{2-n}$, there are a set of diffraction peaks in the range of a 2θ diffraction angle of 7°-13°, and the set of diffraction peaks contain 1-4 main diffraction peaks.

13. The method of claim 1, wherein in the X-ray diffraction pattern of the catalyst carrier $Mg(OR^I)_n(OR^{II})_{2-n}$, there are a first set of diffraction peaks containing 1-4 main diffraction peaks in the range of a 2θ diffraction angle of 5°-15°, and there are a second set of diffraction peaks containing 1-3 main diffraction peaks in the range of a 2θ diffraction angle of 20°-30°.

14. The method of claim 13, wherein in the X-ray diffraction pattern of the catalyst carrier $Mg(OR^I)_n(OR^{II})_{2-n}$, the highest diffraction peak is within the range of the first set of peaks.

15. A method for preparing an olefin polymerization solid catalyst component, comprising:
   (a) obtaining an olefin polymerization catalyst carrier according to the method of claim 1; and
   (b) contacting the olefin polymerization catalyst carrier with a titanium compound having a general formula $TiX_n(OR)_{4-n}$, wherein R is a $C_1$-$C_{20}$ hydrocarbon group, X is a halogen, n=0-4, and at least one electron donor compound.

16. The method of claim 15, wherein the titanium compound is selected from the group consisting of titanium tetrachloride, titanium tetrabromide, titanium tetraiodide and alkoxy titanium halide.

17. The method of claim 16, wherein the titanium compound is titanium tetrachloride.

18. The method of claim 15, wherein the electron donor compound is a compound selected from the group consisting of: phthalate compounds, succinate compounds, 1,3-diether compounds, diol ester compounds, ring-substituted compounds containing an ether group and an acid ester group.

19. The method according to claim 15, wherein contacting said catalyst carrier $Mg(OR^I)_n(OR^{II})_{2-n}$ with the titanium compound and the electro donor compound comprises: contacting the catalyst carrier $Mg(OR^I)_n(OR^{II})_{2-n}$ with the titanium compound and reacting with the donor compound for 1 to 3 hours, and treating the resulting solid product with a titanium compound or a mixed solution containing the titanium compound and an inert organic solvent for 1 to 4 times, and then washing the solid product with an inert organic solvent for 1 to 7 times and dried.

20. The method according to claim 19, wherein the inert organic solvent is a liquid aromatic hydrocarbon or an alkane, the aromatic hydrocarbon is selected from the group consisting of benzene, toluene, xylene, ethylbenzene, propylbenzene and trimethylbenzene, and the alkane is selected from the group consisting of hexane, heptane and cyclohexane.

* * * * *